United States Patent
Horiuchi et al.

(10) Patent No.: US 12,144,665 B2
(45) Date of Patent: Nov. 19, 2024

(54) RADIOGRAPHY APPARATUS

(71) Applicant: FUJIFILM CORPORATION, Tokyo (JP)

(72) Inventors: Hisatsugu Horiuchi, Kanagawa (JP); Yuji Kai, Kanagawa (JP); Yuji Jibiki, Kanagawa (JP); Koji Taninai, Kanagawa (JP); Masataka Sugahara, Kanagawa (JP); Naoyuki Nishino, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 220 days.

(21) Appl. No.: 18/059,984

(22) Filed: Nov. 30, 2022

(65) Prior Publication Data

US 2023/0218245 A1 Jul. 13, 2023

(30) Foreign Application Priority Data

Jan. 12, 2022 (JP) ................................ 2022-003314

(51) Int. Cl.
*A61B 6/04* (2006.01)
*A61B 6/00* (2006.01)
*A61B 6/42* (2024.01)
*A61B 6/46* (2024.01)

(52) U.S. Cl.
CPC .......... *A61B 6/0492* (2013.01); *A61B 6/0407* (2013.01); *A61B 6/4283* (2013.01); *A61B 6/4411* (2013.01); *A61B 6/4452* (2013.01); *A61B 6/462* (2013.01); *A61B 6/463* (2013.01); *A61B 6/488* (2013.01)

(58) Field of Classification Search
CPC .... A61B 6/0492; A61B 6/0407; A61B 6/4283
See application file for complete search history.

(56) References Cited

U.S. PATENT DOCUMENTS

2014/0254762 A1* 9/2014 Yamato .................. A61B 6/541
378/62
2023/0157660 A1* 5/2023 Tu .......................... A61B 6/032
382/128

FOREIGN PATENT DOCUMENTS

JP 2019-180853 A 10/2019

\* cited by examiner

*Primary Examiner* — Hugh Maupin
(74) *Attorney, Agent, or Firm* — SOLARIS Intellectual Property Group, PLLC

(57) ABSTRACT

A radiography apparatus includes an upright imaging stand that is used for radiography on a subject, a camera as a detection sensor that immediately detects a state of the subject with respect to the upright imaging stand, a tablet terminal, and a reflective member. The tablet terminal displays a notification screen including an image output from the camera. The reflective member reflects the notification screen such that the subject facing the upright imaging stand visually recognizes the image.

13 Claims, 17 Drawing Sheets

RADIOGRAPHY APPARATUS

CROSS-REFERENCE TO RELATED APPLICATIONS

The present application claims priority under 35 U.S.C. § 119 to Japanese Patent Application No. 2022-003314, filed on Jan. 12, 2022. The above application is hereby expressly incorporated by reference, in its entirety, into the present application.

BACKGROUND

1. Technical Field

The technology of the present disclosure relates to a radiography apparatus.

2. Description of the Related Art

JP2019-180853A discloses an upright imaging stand provided with a display that displays notification information of radiography to a subject. The upright imaging stand has a support and a holder that holds a radiographic image detector, which detects radiation and outputs a radiographic image, and is moved up and down with respect to the support according to the height of the subject. Paragraph [0019] discloses that, in a case in which a display is provided in the holder, it is better to add a technique of providing a reflective member to reflect notification information such that it is not difficult for the subject to see the displayed notification information.

Examples of the notification information include "Be careful" and "Move" that call attention in a case in which the holder is moved up and down. In addition, examples of the notification information include "Please put your chin on the rest and press your chest" and "Please take a deep breath and hold it" that prompt the subject to prepare for radiography. Alternatively, examples of the notification information include "Radiography is done" and "Thank you for your effort, please leave the room" indicating the end of the radiography. These notification information items are displayed in operative association with an operation of the operator, such as an operation of moving up and down the holder.

SUMMARY

With the recent epidemic of the new coronavirus, it is necessary to avoid contact between an operator and a subject as much as possible even in the field of radiography. In order to avoid the contact between the operator and the subject, a configuration is required in which the subject himself or herself can take a posture suitable for radiography without the intervention of the operator.

JP2019-180853A discloses that a display for displaying notification information to a subject is provided in an upright imaging stand and a reflective member is provided such that it is not difficult for the subject to see the displayed notification information. However, the notification information disclosed in JP2019-180853A is limited to a simple instruction, such as "Please put your chin on the rest and press your chest", that is displayed in operative association with the operation of the operator and does not correspond to the state of the subject with respect to the imaging table. Therefore, this is insufficient as a configuration that enables the subject himself or herself to take a posture suitable for radiography.

One embodiment according to the technology of the present disclosure provides a radiography apparatus in which a display is capable of being provided at the best position where a subject visually recognizes an image, without being bound by restrictions caused by a mechanism of an imaging table, and which enables the subject himself or herself to take a posture suitable for radiography.

According to an aspect of the present disclosure, there is provided a radiography apparatus comprising: an imaging table that is used for radiography on a subject; a detection sensor that detects a state of the subject with respect to the imaging table; a display that displays a notification screen including notification information based on a detection result of the detection sensor; and a reflective member that reflects the notification screen such that the subject facing the imaging table visually recognizes the notification information.

Preferably, the detection sensor is an optical camera that images the subject facing the imaging table, and the notification information is at least one of an image output from the optical camera or a determination result which has been determined on the basis of the image output from the optical camera and which indicates whether or not a posture of the subject is suitable for the radiography.

Preferably, the optical camera includes a first camera that images a back surface of the subject facing the imaging table.

Preferably, the first camera is attached to a radiation source that emits radiation.

Preferably, the optical camera includes a second camera that images a region including a boundary between the imaging table and the subject facing the imaging table.

Preferably, the display is disposed at a position that does not interfere with the subject in a case in which the subject faces the imaging table, and the reflective member is disposed in front of a face of the subject facing the imaging table.

Preferably, the imaging table has a holder that holds a radiographic image detector which detects radiation and which outputs a radiographic image and that is moved in accordance with a physique of the subject, and the display and the reflective member are provided in the holder.

Preferably, the radiography apparatus further comprises an adjustment mechanism that adjusts a position and orientation of the reflective member with respect to the subject.

Preferably, the display is attachable to and detachable from the imaging table.

Preferably, the reflective member is any one of a glass plate or a resin plate having a metal film formed on a surface thereof, a metal plate having a mirror-finished surface, or a plate having a highly reflective film attached thereto.

Preferably, a transparent cover for protecting a surface of the reflective member is provided. Preferably, a frame is attached to an entire periphery of the reflective member.

Preferably, the imaging table is an upright imaging stand used for the radiography on the subject in a standing posture.

According to the technology of the present disclosure, it is possible to provide a radiography apparatus in which a display is capable of being provided at the best position where a subject visually recognizes an image, without being bound by restrictions caused by a mechanism of an imaging table, and which enables the subject himself or herself to take a posture suitable for radiography.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
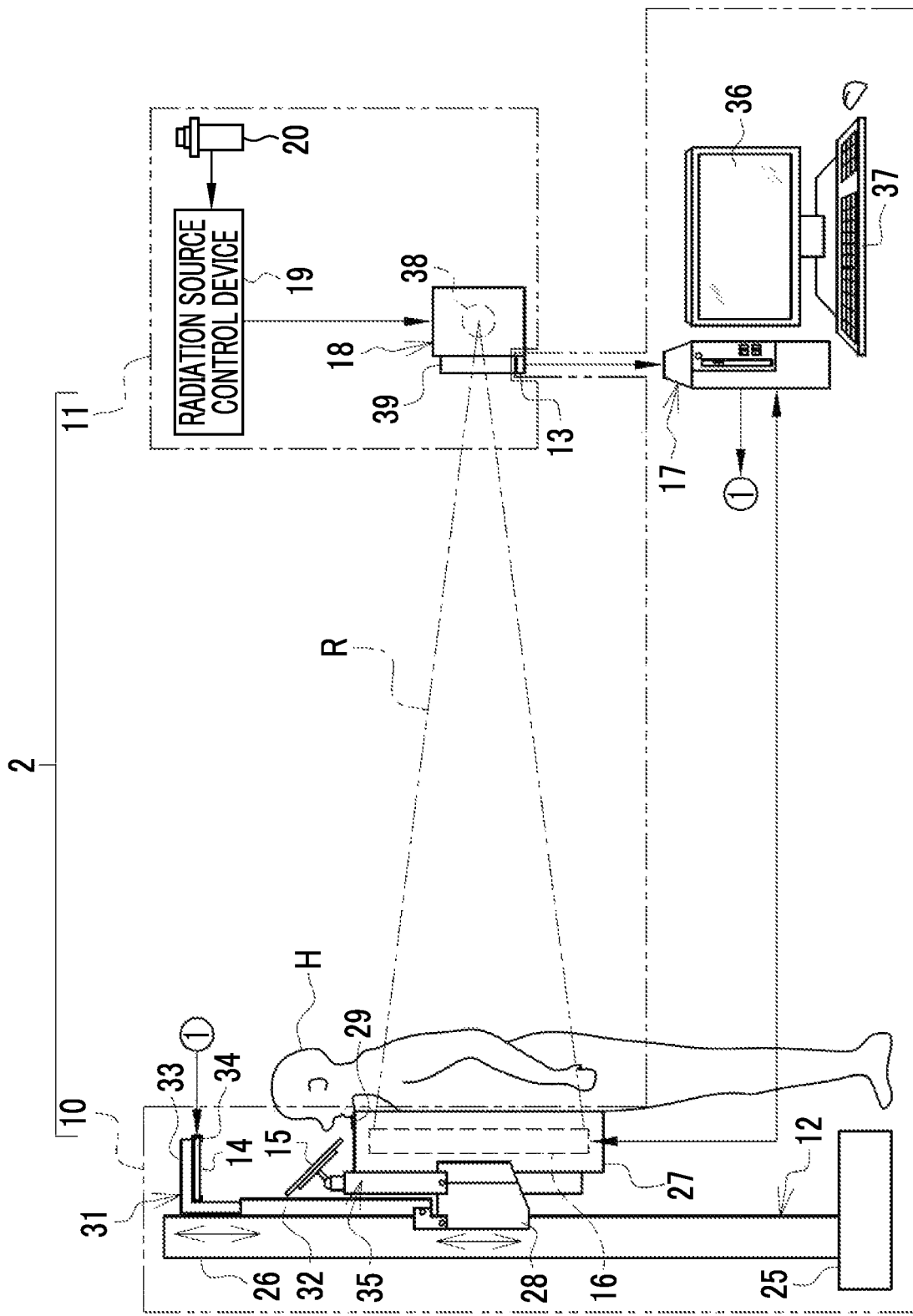
FIG. 1 is a diagram illustrating a radiography system.

For example, as illustrated in FIG. 1, a radiography system 2 is a system that captures a radiographic image of a subject H using radiation R, such as X-rays or y-rays, and includes a radiography apparatus 10 and a radiation generation device 11. The radiography apparatus 10 includes an upright imaging stand 12, a camera 13, a tablet terminal 14, a reflective member 15, an electronic cassette 16, and a console 17. The radiation generation device 11 has a radiation source 18, a radiation source control device 19, and an irradiation switch 20.

Figure 2:
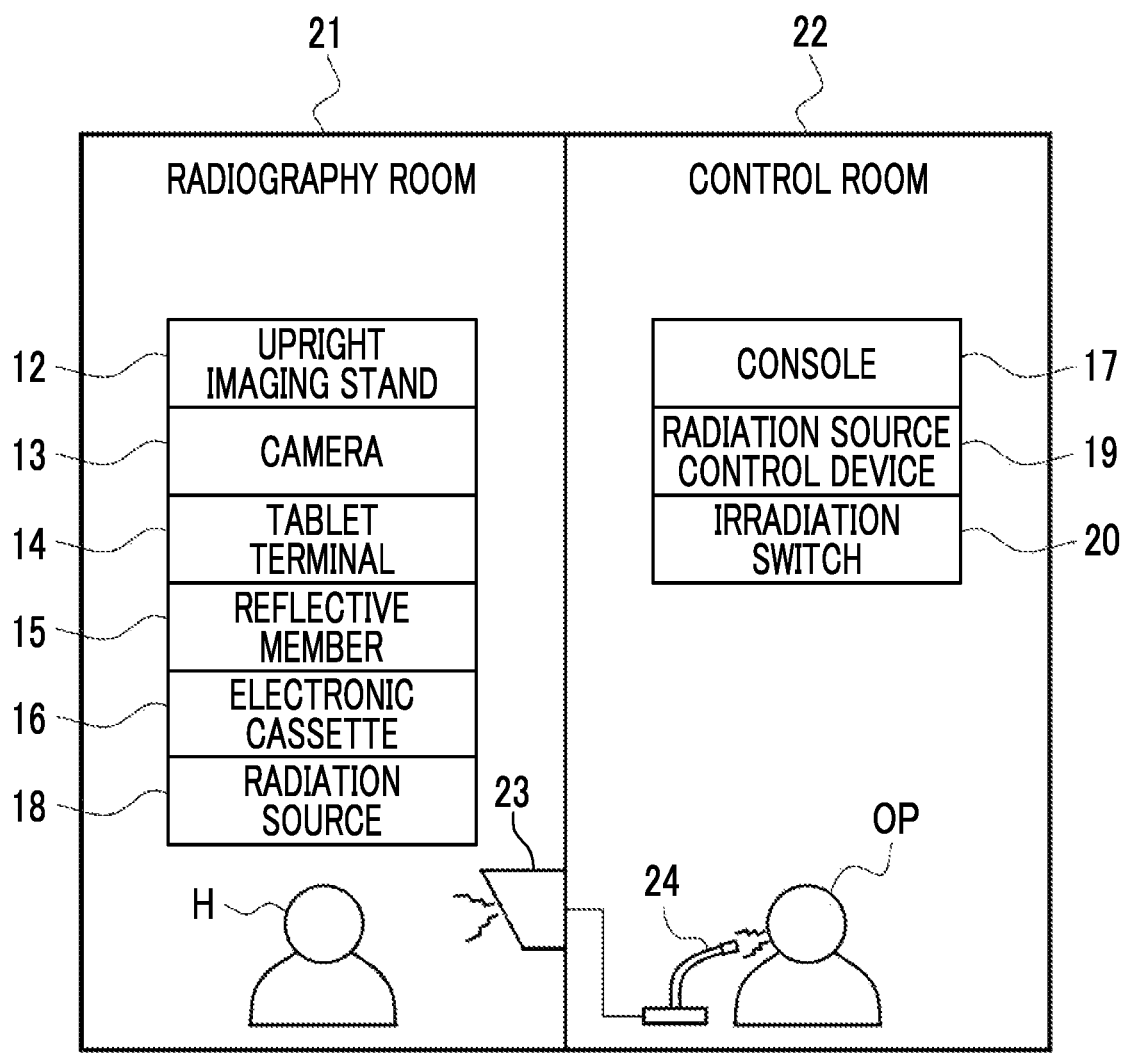
FIG. 2 is a diagram illustrating a radiography room and a control room.

For example, as illustrated in FIG. 2, the upright imaging stand 12, the camera 13, the tablet terminal 14, the reflective member 15, the electronic cassette 16, and the radiation source 18 are installed in a radiography room 21. Meanwhile, the console 17, the radiation source control device 19, and the irradiation switch 20 are installed in a control room 22 adjacent to the radiography room 21. A speaker 23 is installed in the radiography room 21, and a microphone 24 is installed in the control room 22. The speaker 23 outputs a voice which has been uttered by an operator OP in the control room 22 and picked up by the microphone 24. The speaker 23 and the microphone 24 enable the subject H in the radiography room 21 and the operator OP in the control room 22 to communicate with each other. In addition, the speaker is also installed in a waiting room for the subject H. The operator OP makes an announcement to guide the subject H, whose turn for radiography has come, from the waiting room to the radiography room 21 through the speaker and the microphone 24.

Returning to FIG. 1, the upright imaging stand 12 is an imaging table used for radiography on the subject H in a standing posture. The upright imaging stand 12 has a pedestal 25 that is installed on a floor of the radiography room 21, a support 26 that extends in a height direction from the pedestal 25, and a holder 27 that holds the electronic cassette 16 therein. The holder 27 is connected to the support 26 through a connection portion 28 and is moved up and down with respect to the support according to the height of the subject H. The moving up and down of the holder 27 can be performed from the control room 22 through the console 17. The holder 27 is provided with a chin rest portion 29 (see also FIG. 3) with which the chin of the subject H standing in front of the upright imaging stand 12 comes into contact.

The camera 13 is a digital camera that captures a digital image. The camera 13 is attached to the radiation source 18, specifically, to the side of an irradiation field limiter 39 of the radiation source 18 and images a back surface (back) of the subject H standing in front of the upright imaging stand 12. The camera 13 is an example of a "detection sensor", an "optical camera", and a "first camera" according to the technology of the present disclosure. The camera 13 outputs a captured image 71 (see FIG. 8) to the console 17. The image 71 is an example of a "detection result of the detection sensor" and "notification information" according to the technology of the present disclosure. As described above, the "notification information" according to the technology of the present disclosure also includes the "detection result of the detection sensor". In addition, the camera 13 may be provided in the irradiation field limiter 39.

Figure 3:
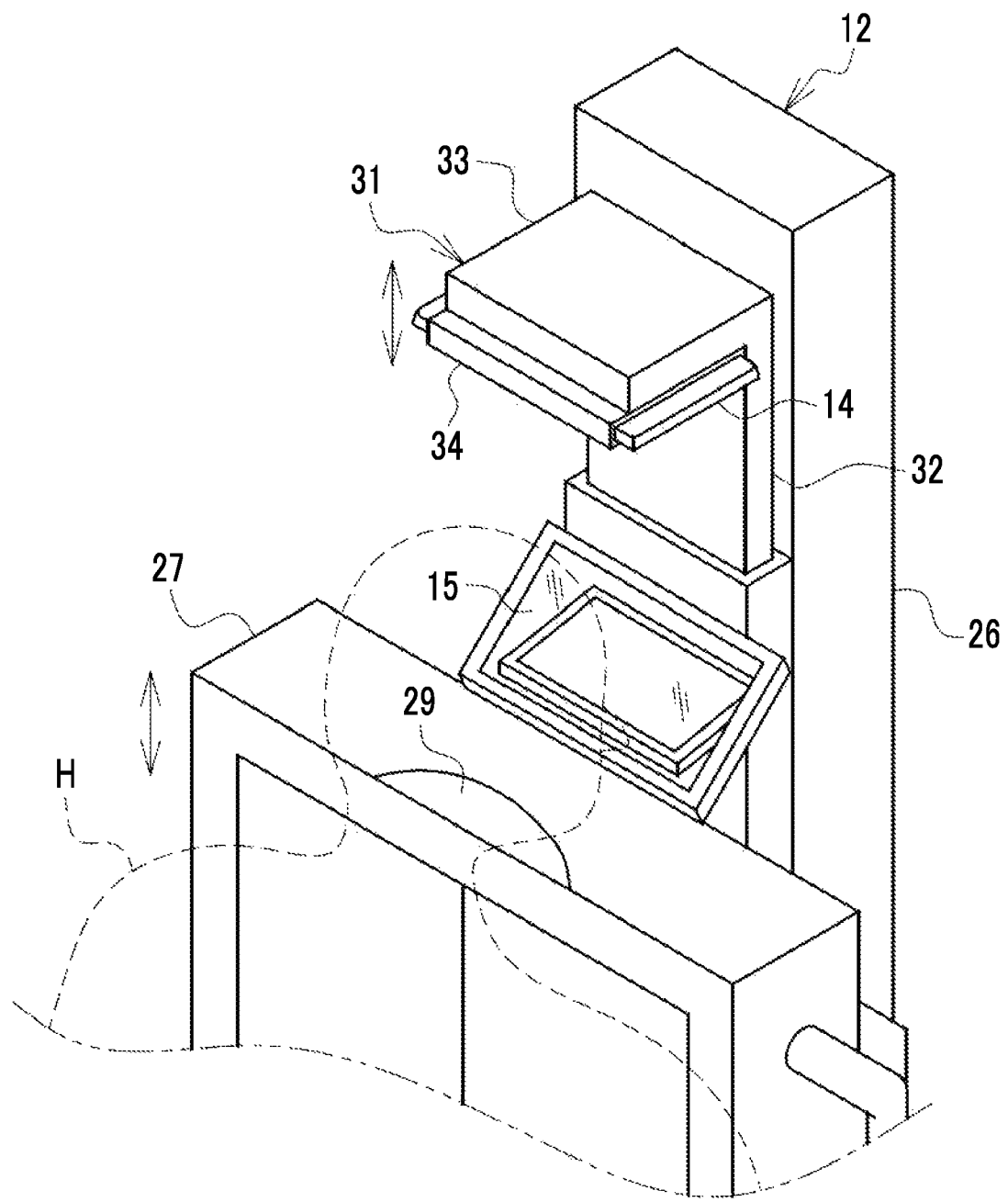
FIG. 3 is a perspective view illustrating the vicinity of a holder of an upright imaging stand.
Figure 8:
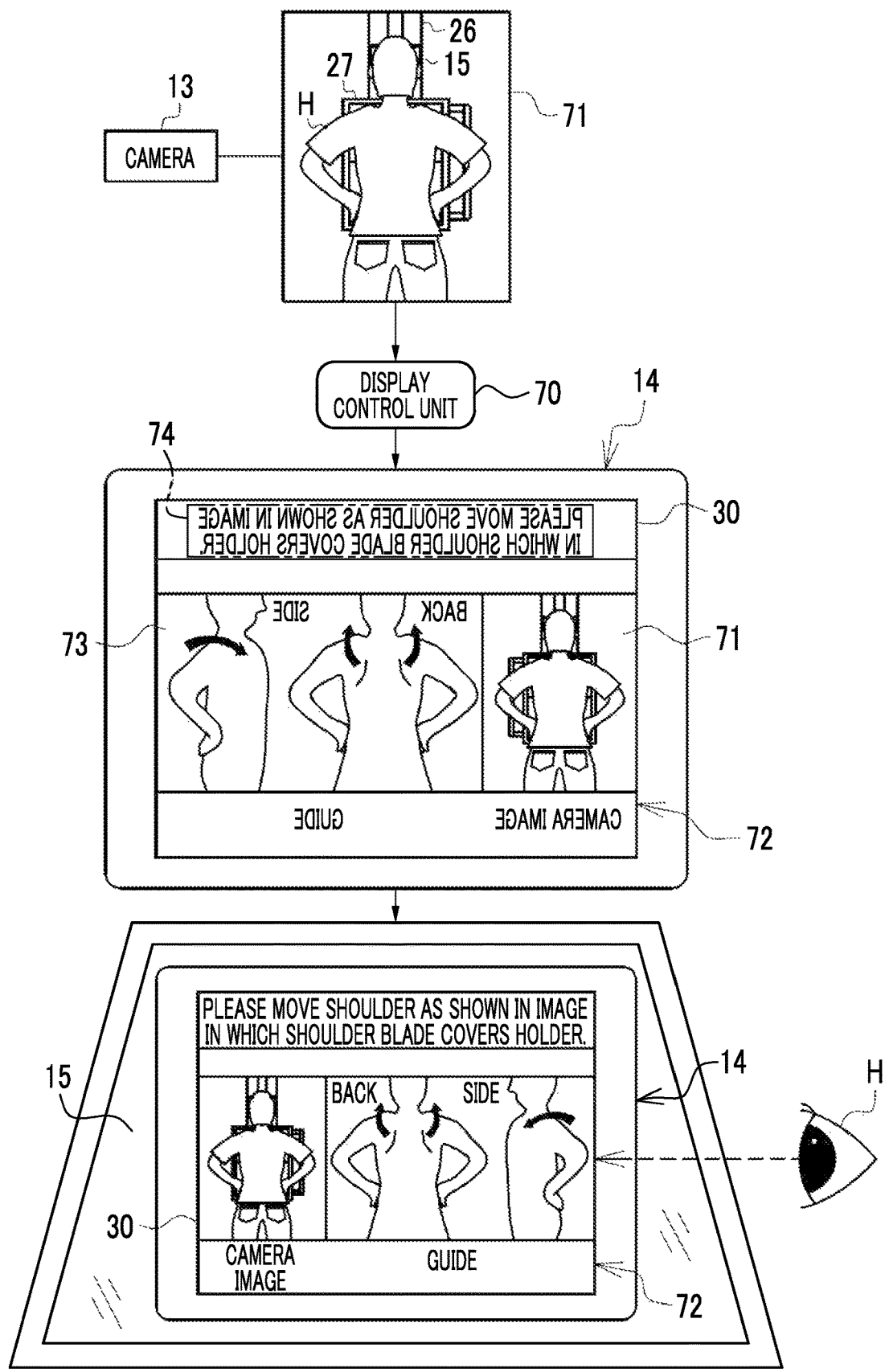
FIG. 8 is a diagram illustrating a process of a display control unit of a CPU of the console and a notification screen.

The tablet terminal 14 comprises a touch panel display 30 (see FIG. 8). As illustrated in FIG. 3, the tablet terminal 14 is attached to a bracket 31. The bracket 31 is connected to the connection portion 28. Therefore, the tablet terminal 14 is moved up and down in operative association with the moving up and down of the connection portion 28 and thus the holder 27.

The bracket 31 has a first portion 32, a second portion 33, and a terminal holder 34. The first portion 32 extends in the height direction like the support 26. The second portion 33 is bent by 90° in the horizontal direction from the first portion 32 to the holder 27. The terminal holder 34 is attached to a surface of the second portion 33 which faces the head of the subject H. The terminal holder 34 holds the tablet terminal 14 with the touch panel display 30 facing downward. Therefore, the tablet terminal 14 is disposed above the head of the subject H which is a position that does not interfere with the subject H in a case in which the subject H stands in front of the upright imaging stand 12. The tablet terminal 14 displays a notification screen 72 (see FIG. 8) including the image 71 output from the camera 13 on the touch panel display 30. The tablet terminal 14 is an example of a "display" according to the technology of the present disclosure.

The reflective member 15 is attached to a bracket 35. The bracket 35 is attached to the connection portion 28. Therefore, the reflective member 15 is moved up and down in operative association with the moving up and down of the connection portion 28 and thus the holder 27 like the tablet terminal 14.

The bracket 35 is vertically provided in a central portion between the support 26 and the holder 27. The height of the bracket 35 is slightly larger than that of the holder 27. Therefore, the reflective member 15 is disposed in front of the face of the subject H standing in front of the upright imaging stand 12. The reflective member 15 is inclined upward (on the side of the tablet terminal 14) by about 45° with respect to the line of sight of the subject H.

Since the reflective member 15 is disposed in front of the face of the subject H, the reflective member 15 is exposed to the breath of the subject H during radiography. Therefore, whenever the subject H is replaced, the reflective member 15 is manually disinfected by the operator OP with a disinfectant such as alcohol or hypochlorous acid water.

The electronic cassette 16 is a portable radiographic image detector that outputs a radiographic image corresponding to the radiation R transmitted through the subject H. The electronic cassette 16 is connected to the console 17 such that it can communicate with the console 17 wirelessly or in a wired manner. The electronic cassette 16 is accommodated in the holder 27 of the upright imaging stand 12 and is then used. In addition, the electronic cassette 16 can be removed from the holder 27, stood up against the subject H or inserted under the subject H lying on a bed in a hospital room, and then used. The electronic cassette 16 is an example of a "radiographic image detector" according to the technology of the present disclosure.

The electronic cassette 16 has a detection panel in which a plurality of pixels accumulating charge corresponding to the radiation R are arranged in a two-dimensional matrix. The detection panel is also called a flat panel detector (FPD). The electronic cassette 16 has a function of detecting the start and end of the emission of the radiation R. In a case in which the start of the emission of the radiation R is detected, the detection panel starts an accumulation operation of accumulating charge in the pixels. In a case in which the end of the emission of the radiation R is detected, the detection panel starts a reading operation of reading the charge accumulated in the pixels as an electric signal.

In addition, the electronic cassette 16 and the radiation source control device 19 may be connected such that they can communicate with each other, and synchronizing signals indicating the start and end of the emission of the radiation R may be exchanged between the electronic cassette 16 and the radiation source control device 19 to synchronize the emission start timing of the radiation R and the start timing of the accumulation operation and to synchronize the emission end timing of the radiation R and the start timing of the reading operation.

The console 17 is, for example, a desktop personal computer and has a display 36 that displays various screens and an input device 37 that includes a keyboard, a mouse, and the like and receives operation instructions from the operator OP. The console 17 transmits various signals to the electronic cassette 16. In addition, the console 17 receives a radiographic image from the electronic cassette 16. The console 17 displays the radiographic image on the display 36. In addition, the console 17 may be a notebook personal computer.

The radiation source 18 has a radiation tube 38 and the irradiation field limiter 39. The radiation tube 38 is provided with, for example, a filament, a target, and a grid electrode (none of which are illustrated). A voltage is applied between the filament, which is a cathode, and the target, which is an anode. The voltage applied between the filament and the target is called a tube voltage. The filament emits thermoelectrons corresponding to the applied tube voltage to the target. The target emits the radiation R by the collision of the thermoelectrons from the filament. The grid electrode is disposed between the filament and the target. The grid electrode changes the flow rate of the thermoelectrons from the filament to the target according to the applied voltage. The flow rate of the thermoelectrons from the filament to the target is called a tube current.

The irradiation field limiter 39 is also called a collimator and limits an irradiation field of the radiation R emitted from the radiation tube 38. For example, the irradiation field limiter 39 has a configuration in which four shielding plates made of lead or the like that shields the radiation R are disposed on each side of a quadrangle and a quadrangular emission opening for transmitting the radiation R is formed in a central portion. The irradiation field limiter 39 changes the position of each shielding plate to change the size of the emission opening, thereby changing the irradiation field of the radiation R.

The horizontal position of the radiation source 18 can be changed by a movement mechanism including a rail or a carriage (not illustrated). In addition, the height position of the radiation source 18 can be changed by a telescopic arm. The change of the horizontal position and the height position of the radiation source 18 can be performed from the control room 22 through the radiation source control device 19.

The radiation source 18 and the irradiation switch 20 are connected to the radiation source control device 19. The radiation source control device 19 controls the operation of the radiation source 18 in response to various command signals from the irradiation switch 20. The irradiation switch 20 is operated in a case in which the operator OP instructs the radiation source 18 to start the emission of the radiation R.

The operator OP sets the irradiation conditions of the radiation R in the radiation source control device 19. The irradiation conditions are a tube voltage applied to the radiation tube 38, a tube current, and an irradiation time of the radiation R. In a case in which the irradiation switch 20 is operated to input an instruction to start the emission of the radiation R, the radiation source control device 19 directs the radiation tube 38 to emit the radiation R under the set irradiation conditions. In a case in which the irradiation time set in the irradiation conditions has elapsed since the start of the emission of the radiation R, the radiation source control device 19 stops the emission of the radiation R from the radiation tube 38. Alternatively, the emission of the radiation R may be ended by an auto exposure control (AEC) function. The AEC function is a function that detects the dose of the radiation R during the emission of the radiation R and stops the emission of the radiation R from the radiation tube 38 at the time when an integrated value of the detected dose (cumulative dose) reaches a preset target dose. In this case, the detection panel starts the reading operation in a case in which the cumulative dose of the radiation R reaches the target dose. In addition, the irradiation condition may be a tube current-irradiation time product which is a product of the tube current and the irradiation time.

Figure 4:
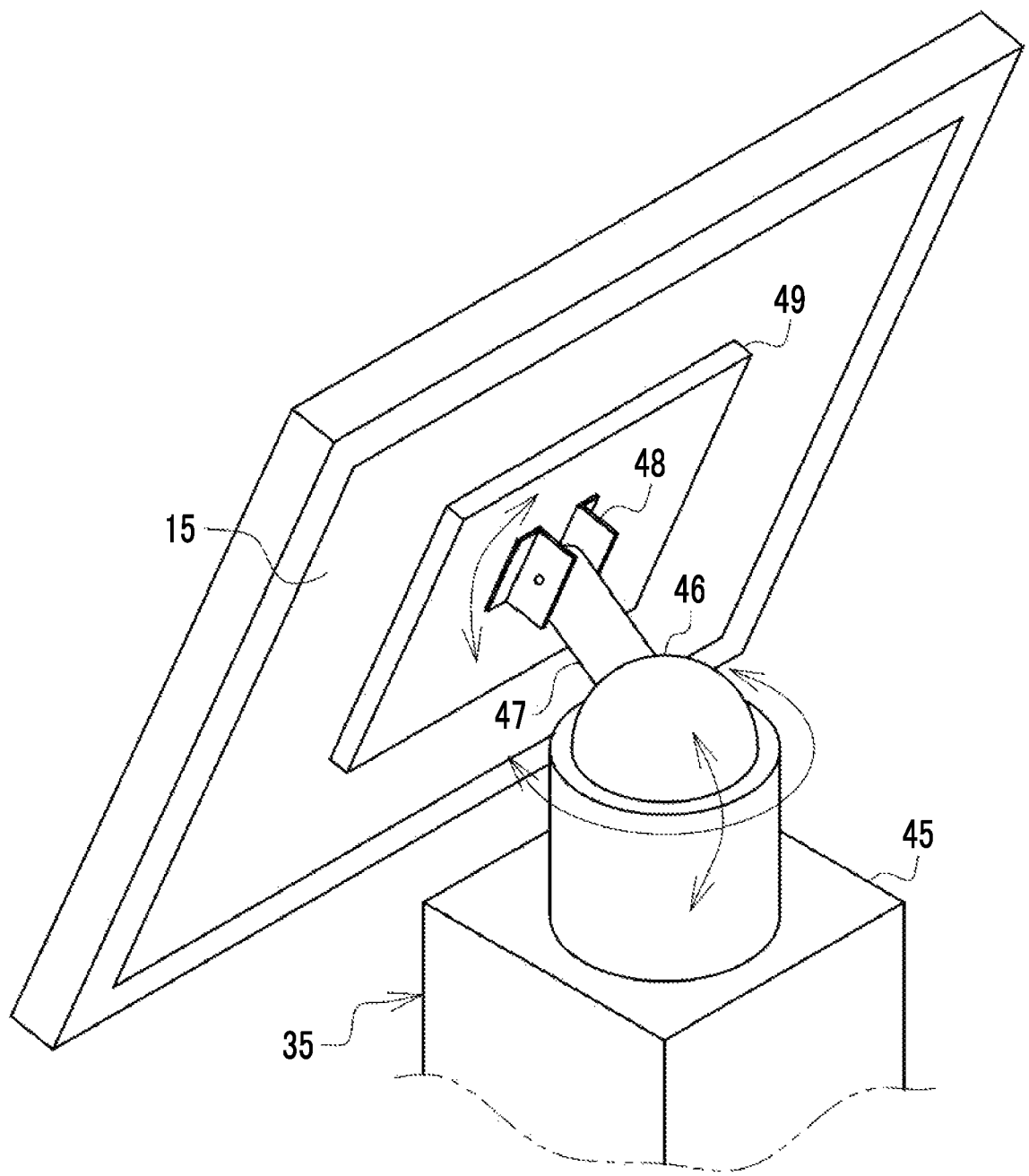
FIG. 4 is a perspective view illustrating a reflective member and an adjustment mechanism.

For example, as illustrated in FIG. 4, the bracket 35 includes a support 45, a ball joint 46, an arm 47, an angle adjuster 48, and an attachment plate 49. The support 45 is provided in a central portion between the support 26 and the holder 27 and extends in the height direction. The ball joint 46 is provided on the support 45. One end of the arm 47 is connected to the ball joint 46, and the other end of the arm 47 is connected to the attachment plate 49 through the angle adjuster 48. A back surface of the reflective member 15 is attached to the attachment plate 49. The reflective member 15 can be rotated in the up, down, left, and right directions by the ball joint 46. In addition, the orientation of the reflective member 15 in the vertical direction can be finely adjusted by the angle adjuster 48. The ball joint 46 and the angle adjuster 48 are an example of an "adjustment mechanism" according to the technology of the present disclosure.

Figure 5:
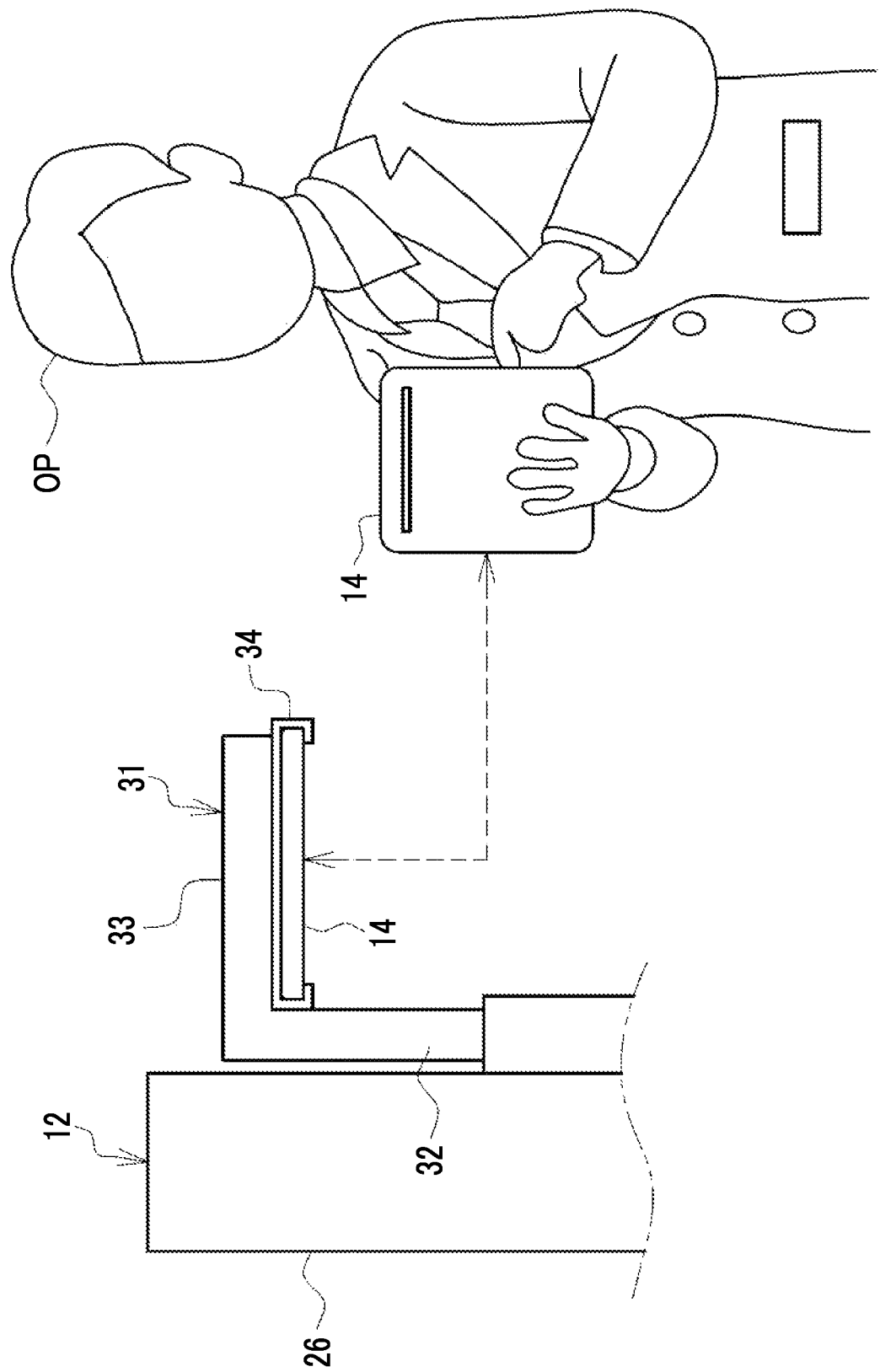
FIG. 5 is a diagram illustrating that a tablet terminal can be attached to and detached from a terminal holder.

For example, as illustrated in FIG. 5, the tablet terminal 14 can be attached to and detached from the terminal holder 34. A screen for setting the irradiation conditions of the radiation R is displayed or a radiographic image is displayed on the tablet terminal 14 removed from the terminal holder 34, and the tablet terminal 14 is used as a simple console by the operator OP.

Figure 6:
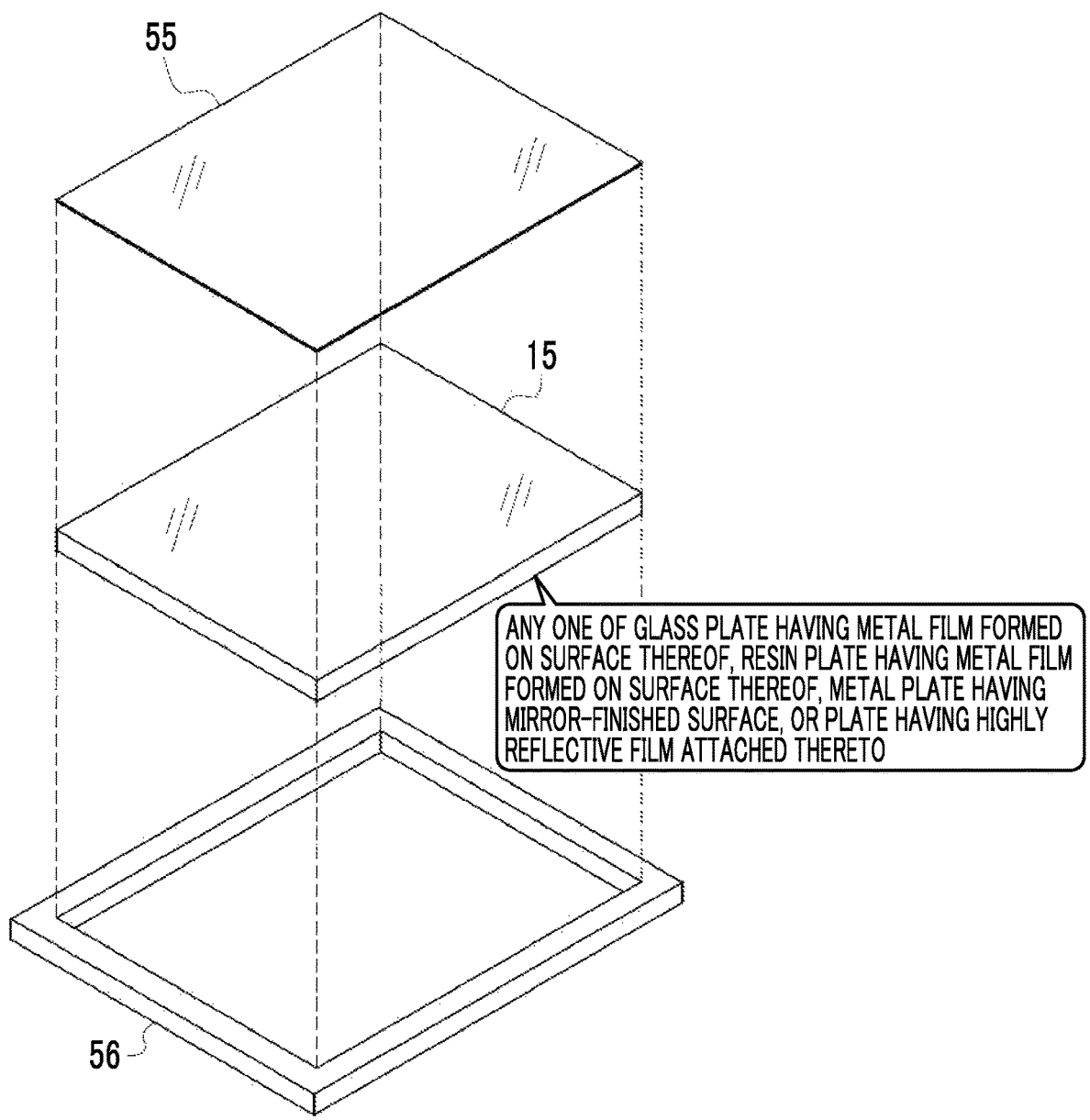
FIG. 6 is an exploded perspective view illustrating a cover, a reflective member, and a frame.

For example, as illustrated in FIG. 6, the reflective member 15 is any one of a glass plate or a resin plate having a metal film, such as a silver film or an aluminum film, formed on a surface thereof, a metal plate having a mirror-finished surface, or a plate having a highly reflective film attached thereto. A transparent cover 55 is attached to a surface of the reflective member 15. The cover 55 is made of a resin, such as polycarbonate or acrylic, or tempered glass whose surface strength has been increased by quenching. Further, a frame 56 is attached to the entire periphery of the reflective member 15. The cover 55 protects the surface of the reflective member 15. In addition, the frame 56 protects the entire peripheral edge of the reflective member 15.

Figure 7:
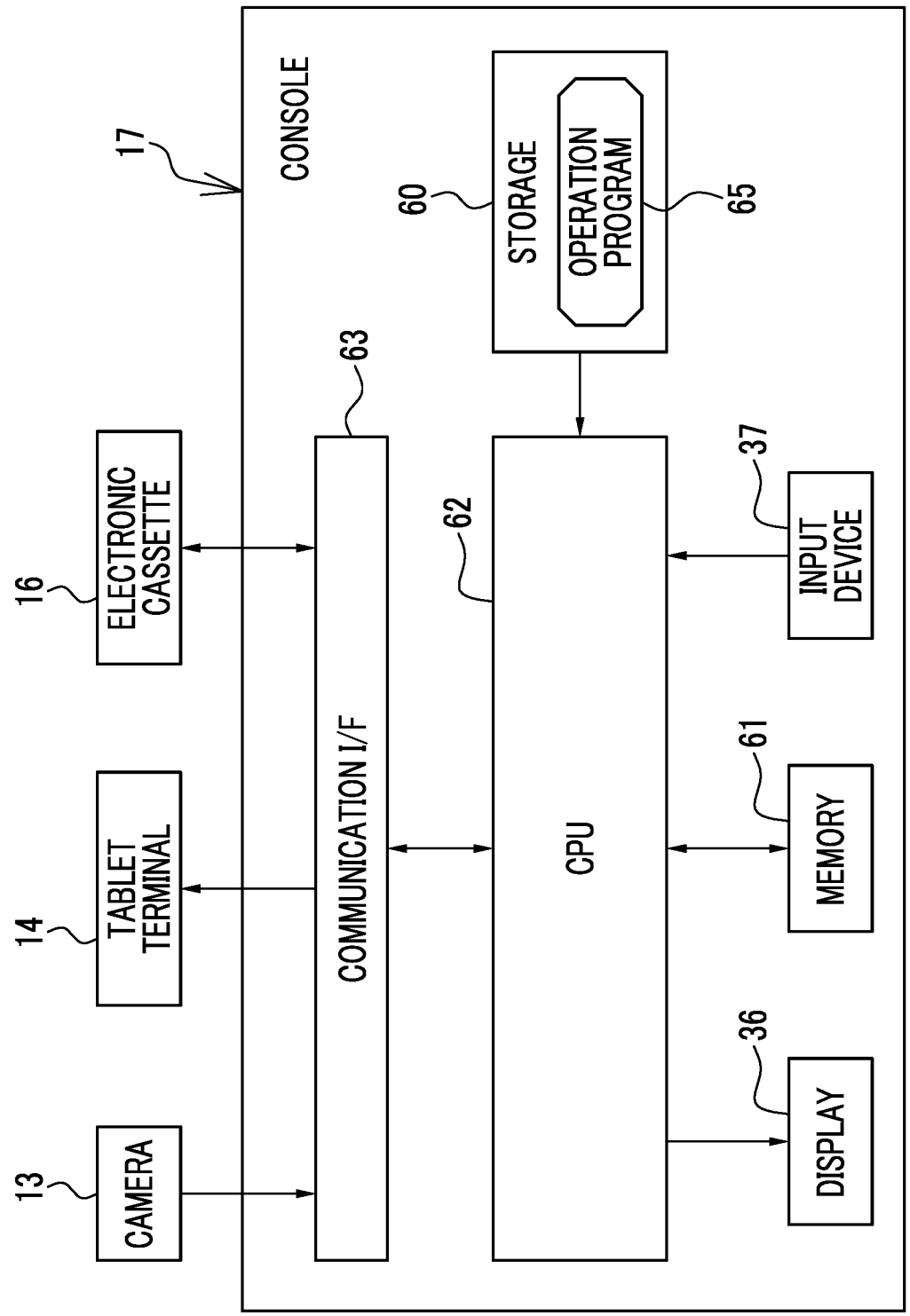
FIG. 7 is a block diagram illustrating an internal configuration of a console.

For example, as illustrated in FIG. 7, the console 17 comprises a storage 60, a memory 61, a central processing unit (CPU) 62, and a communication interface (I/F) 63 in addition to the display 36 and the input device 37. The display 36, the input device 37, the storage 60, the memory 61, the CPU 62, and the communication I/F 63 are connected to each other through a bus line (not illustrated).

The storage 60 is a hard disk drive that is provided in the computer constituting the console 17 or is connected to the computer through a cable or a network. The storage 60 stores, for example, a control program, such as an operating system, various application programs including an operation program 65, and various kinds of data associated with these programs. The operation program 65 is an application program for causing the computer to function as the console 17. In addition, a solid state drive may be used instead of the hard disk drive.

The memory 61 is a work memory used by the CPU 62 to perform processes. The CPU 62 loads the program stored in the storage 60 to the memory 61 and performs a process corresponding to the program. Therefore, the CPU 62 controls the overall operation of each unit of the computer. In addition, the memory 61 may be provided in the CPU 62. The communication I/F 63 controls the transmission of various kinds of information to external devices such as the camera 13, the tablet terminal 14, and the electronic cassette 16.

For example, as illustrated in FIG. 8, in a case in which the operation program 65 is started, the CPU 62 of the computer constituting the console 17 functions as a display control unit 70 in cooperation with the memory 61 and the like. The display control unit 70 acquires the image 71 output from the camera 13. The image 71 includes the back surface of the subject H standing in front of the upright imaging stand 12.

The display control unit 70 performs control to display the notification screen 72 on the touch panel display 30 of the tablet terminal 14. The notification screen 72 includes the image 71, a guide illustration 73, and a guide message 74. All of the images 71, the guide illustration 73, and the guide message 74 are mirror-inverted such that they are reflected in a normal direction in a case in which they are reflected by the reflective member 15. The display control unit 70 displays the image 71 output from the camera 13 at a predetermined frame rate on the notification screen 72 while sequentially updating the image 71. That is, the image 71 displayed on the notification screen 72 is a live view image. The guide illustration 73 and the guide message 74 have content that prompts the subject H to open the shoulder blade so as to cover the holder 27 and to bring the chest into close contact with the holder 27.

A mirror image of the tablet terminal 14 held by the terminal holder 34 is reflected in the reflective member 15 in a posture in which a surface of the touch panel display 30 is parallel to the horizontal direction (see also FIG. 3). The reflective member 15 reflects the touch panel display 30 of the tablet terminal 14 and thus the notification screen 72 such that the subject H standing in front of the upright imaging stand 12 can visually recognize, for example, the image 71.

Next, the operation of the above configuration will be described. Before radiography, the operator OP performs an imaging preparation operation. The imaging preparation operation includes the setting of the irradiation conditions of the radiation R and the adjustment of the positions and postures (positioning) of the electronic cassette 16, the radiation source 18, and the subject H. The operator OP operates the radiation source control device 19 in the control room 22 to set the irradiation conditions of the radiation R corresponding to the radiography to be performed. Next, the operator OP transmits an announcement to the speaker in the waiting room through the microphone 24 to guide the subject H from the waiting room to the radiography room 21.

The operator OP transmits an announcement to the speaker 23 of the radiography room 21 through the microphone 24 such that the subject H stands in front of the upright imaging stand 12. The operator OP operates the console 17 to move up and down the holder 27 and thus the electronic cassette 16 according to the height of the subject H to adjust the height position of the electronic cassette 16. With a change in the height position of the electronic cassette 16, the radiation source 18 is automatically moved up and down. The radiation source 18 is moved to a height position corresponding to the height position of the electronic cassette 16. This function of automatically changing the height position of the radiation source 18 in operative association with the change of the height position of the electronic cassette 16 is called an auto-tracking function. In this case, the horizontal position of the radiation source 18 may be further adjusted. In addition, contrary to the auto-tracking function, a reverse tracking function that automatically changes the height position of the electronic cassette 16 in operative association with the change of the height position of the radiation source 18 may be adopted.

The operator OP transmits an announcement to the speaker 23 of the radiography room 21 through the microphone 24. That is, the subject H is prompted to place the chin on the chin rest portion 29, to place the hands on the waist, to project the elbows forward, to open the shoulder blades to cover the holder 27, and to bring the chest into close contact with the holder 27.

During the positioning of the electronic cassette 16, the radiation source 18, and the subject H, the camera 13 images the back surface of the subject H standing in front of the upright imaging stand 12. The image 71 captured by the camera 13 is output to the console 17.

As illustrated in FIG. 8, in the console 17, the display control unit 70 constructed in the CPU 62 acquires the image 71 from the camera 13. The notification screen 72 including, for example, the image 71 is generated under the control of the display control unit 70. The notification screen 72 is displayed on the touch panel display 30 of the tablet terminal 14. The touch panel display 30 of the tablet terminal 14 and thus the notification screen 72 are reflected by the reflective member 15 and are visually recognized by the subject H standing in front of the upright imaging stand 12. The subject H himself or herself takes a posture suitable for radiography while looking at the notification screen 72 with reference to the announcement from the operator OP.

After the positioning of the electronic cassette 16, the radiation source 18, and the subject H is completed, the operator OP transmits an announcement to the speaker 23 in the radiography room 21 through the microphone 24 to instruct the subject H to take a deep breath and to hold it. Then, the operator OP operates the irradiation switch 20 to instruct the radiation source 18 to start the emission of the radiation R. Then, the radiation R is emitted from the radiation source 18 to the subject H.

The radiation R transmitted through the subject H reaches the electronic cassette 16. Then, the electronic cassette 16 detects the radiation R as a radiographic image. The radiographic image is transmitted from the electronic cassette 16 to the console 17. The console 17 performs various types of image processing on the radiographic image from the electronic cassette 16. Then, the radiographic image is displayed on the display 36.

As described above, the radiography apparatus 10 comprises the upright imaging stand 12 used for radiography on the subject H, the camera 13 as a detection sensor that immediately detects the state of the subject H with respect to the upright imaging stand 12, the tablet terminal 14, and the reflective member 15. The tablet terminal 14 displays the notification screen 72 including the image 71 output from the camera 13. The reflective member 15 reflects the notification screen 72 such that the subject H standing in front of the upright imaging stand 12 can visually recognize the image 71.

As a method of causing the subject H to visually recognize the notification screen 72, first, a method that simply installs the tablet terminal 14 in front of the face of the subject H is considered. However, in this method, unless an appropriate distance is provided between the subject H and the tablet terminal 14, it is difficult for the subject H to visually recognize the notification screen 72. For example, in a case in which the distance between the support 26 and the holder 27 increases in order to provide an appropriate distance between the subject H and the tablet terminal 14, a weight balance between the support 26 and the holder 27 is lost. Therefore, it is necessary to increase the size of the pedestal 25, or a large load is applied to the moving up and down of the connection portion 28, which causes various inconveniences. For this reason, it is not possible to adopt the method that installs the tablet terminal 14 in front of the face of the subject H. Therefore, in the technology of the present disclosure, the tablet terminal 14 is disposed above the head of the subject H, and the notification screen 72 is reflected by the reflective member 15 such that the subject H can visually recognize the notification screen 72. As a result, it is possible to provide the tablet terminal 14 at the best position where the subject H visually recognizes the notification screen, without being bound by the restrictions caused by the mechanism of the upright imaging stand 12, such as the weight balance between the support 26 and the holder 27.

In addition, the notification information disclosed in JP2019-180853A is limited to a simple instruction, such as "Please put your chin on the rest and press your chest", that is displayed in operative association with the operation of the operator. In contrast, in the technology of the present disclosure, the notification screen 72 including the image 71, which is the detection result of immediately detecting the state of the subject H with respect to the upright imaging stand 12, is displayed. Therefore, the subject H himself or herself can take a posture suitable for radiography without the intervention of the operator OP. As a result, it is possible to avoid the contact between the operator OP and the subject H.

In this embodiment, the camera 13 that images the subject H standing in front of the upright imaging stand 12 is given as an example of the detection sensor, and the image 71 output from the camera 13 is given as an example of the notification information. The image 71 enables the subject H to immediately understand the position and posture of the subject H with respect to the upright imaging stand 12. Therefore, the subject H can easily take a posture suitable for radiography.

In addition, in this embodiment, the camera 13 that images the back surface of the subject H standing in front of the upright imaging stand 12 is given as an example of the optical camera. As a matter of course, it is difficult for the subject H to visually recognize the back surface of the subject H. Therefore, the image 71 is notification information that is useful for the subject H himself or herself to take a posture suitable for radiography. The subject H can check, for example, the position of the subject H with respect to the holder 27 and thus the electronic cassette 16 or the degree of opening of the shoulder blade using the image 71.

As illustrated in FIG. 1, the camera 13 is attached to the radiation source 18 that emits the radiation R. In general, the radiation source 18 is disposed at a position facing the upright imaging stand 12. Therefore, in a case in which the camera 13 is attached to the radiation source 18, it is possible to easily image the back surface of the subject H standing in front of the upright imaging stand 12.

As illustrated in FIG. 3, the tablet terminal 14 is disposed above the head of the subject H which is a position where the tablet terminal 14 does not interfere with the subject H in a case in which the subject H stands in front of the upright imaging stand 12. Therefore, the tablet terminal 14 does not get in the way of the subject H in a case in which the subject H stands in front of the upright imaging stand 12. In addition, the reflective member 15 is disposed in front of the face of the subject H standing in front of the upright imaging stand 12. Therefore, the subject H can visually recognize, for example, the image 71 in a natural posture of standing in front of the upright imaging stand 12 without performing extra movements such as tilting the head or turning the line of sight obliquely.

The upright imaging stand 12 has the holder 27 that holds the electronic cassette 16 which detects the radiation R and outputs a radiographic image and is moved up and down according to the height of the subject H. Then, the tablet terminal 14 and the reflective member 15 are provided in the holder 27. Therefore, the tablet terminal 14 and the reflective member 15 can be easily set to the height position corresponding to the height of the subject H only by moving up and down the holder 27. Further, it is not necessary to provide an elevating mechanism for the tablet terminal 14 and the reflective member 15 separately from the holder 27.

As illustrated in FIG. 4, the ball joint 46 and the angle adjuster 48 are provided as the adjustment mechanism that adjusts the position and orientation of the reflective member 15 with respect to the subject H. Therefore, it is possible to adjust the position and orientation of the reflective member 15 according to, for example, the position of the eyes of the subject H and the effect such that the subject H can easily see the image 71 and the like. In addition, the adjustment mechanism is not limited to the ball joint 46 and the angle adjuster 48 given as an example.

As illustrated in FIG. 5, the tablet terminal 14 is attachable to and detachable from the imaging table. Therefore, the tablet terminal 14 can be used not only for displaying the notification screen 72 but also for other purposes such as a simple console.

As illustrated in FIG. 6, the reflective member 15 is any one of a glass plate or a resin plate having a metal film formed on a surface thereof, a metal plate having a mirror-finished surface, or a plate having a highly reflective film attached thereto. Here, considering that the reflective member 15 is disinfected with a disinfectant, such as alcohol or hypochlorous acid water, whenever the subject H is replaced, the reflective member 15 having resistance to the disinfectant is preferable. From this point of view, since a whitening component is precipitated in the glass plate by an acidic disinfectant typified by hypochlorous acid water, it is difficult to see the glass plate. Therefore, it is more preferable that the reflective member 15 is a resin plate having a metal film formed on a surface thereof or a metal plate having a mirror-finished surface.

As illustrated in FIG. 6, the transparent cover 55 for protecting the surface of the reflective member 15 is provided. Therefore, it is possible to suppress deterioration such as scratches, cracks, or fogging caused by the disinfectant on the surface of the reflective member 15. Further, the frame 56 is attached to the entire periphery of the reflective member 15. Therefore, it is possible to prevent the scattering of the reflective member 15 to the surroundings in a case in which the reflective member 15 is cracked. The reflective member 15 which is difficult to see due to the precipitation of the whitening component can be removed from the frame 56 to be easily replaced with a new reflective member 15. In addition, the cover 55 may be attached to the frame 56 instead of directly attaching the cover 55 to the surface of the reflective member 15.

In this embodiment, the upright imaging stand 12 used for radiography on the subject H in the standing posture is given as an example of the imaging table. The upright imaging stand 12 is frequently used for radiography such as chest radiography or abdominal radiography. Therefore, it is possible to fully exhibit the effect that the subject H himself or herself can take a posture suitable for radiography.

2_1st Embodiment

Figure 9:
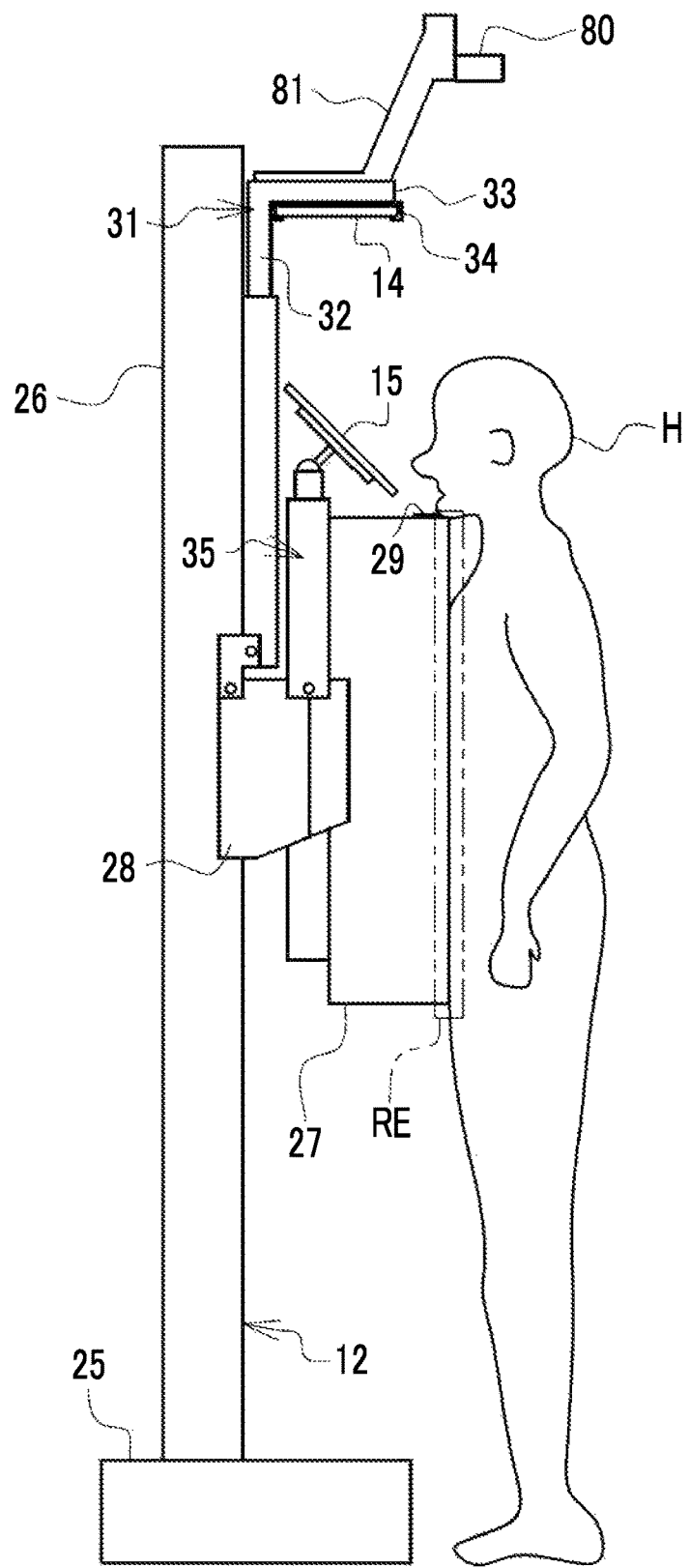
FIG. 9 is a diagram illustrating an upright imaging stand according to a 2_1st embodiment.

For example, as illustrated in FIG. 9, in a 2_1st embodiment, in addition to the camera 13, a camera 80 that images a region RE including a boundary between the upright imaging stand 12 and the subject H standing in front of the upright imaging stand 12 is provided. The camera 80 is an example of the "detection sensor", the "optical camera", and the "second camera" according to the technology of the present disclosure.

The camera 80 is attached to a bracket 81. One end of the bracket 81 is attached to a surface of the second portion 33 of the bracket 31 which is opposite to the surface to which the terminal holder 34 is attached. The other end of the bracket 81 protrudes obliquely upward from the second portion 33 of the bracket 31 to the holder 27. The camera 80 is attached to the other end of the bracket 81. The amount of protrusion of the other end of the bracket 81 obliquely upward is set such that the second portion 33, the terminal holder 34, and the tablet terminal 14 fall within the angle of view of the camera 80. Similarly to the tablet terminal 14 and the reflective member 15, the camera 80 is moved up and down in operative association with the moving up and down of the connection portion 28 and thus the holder 27.

Figure 10:
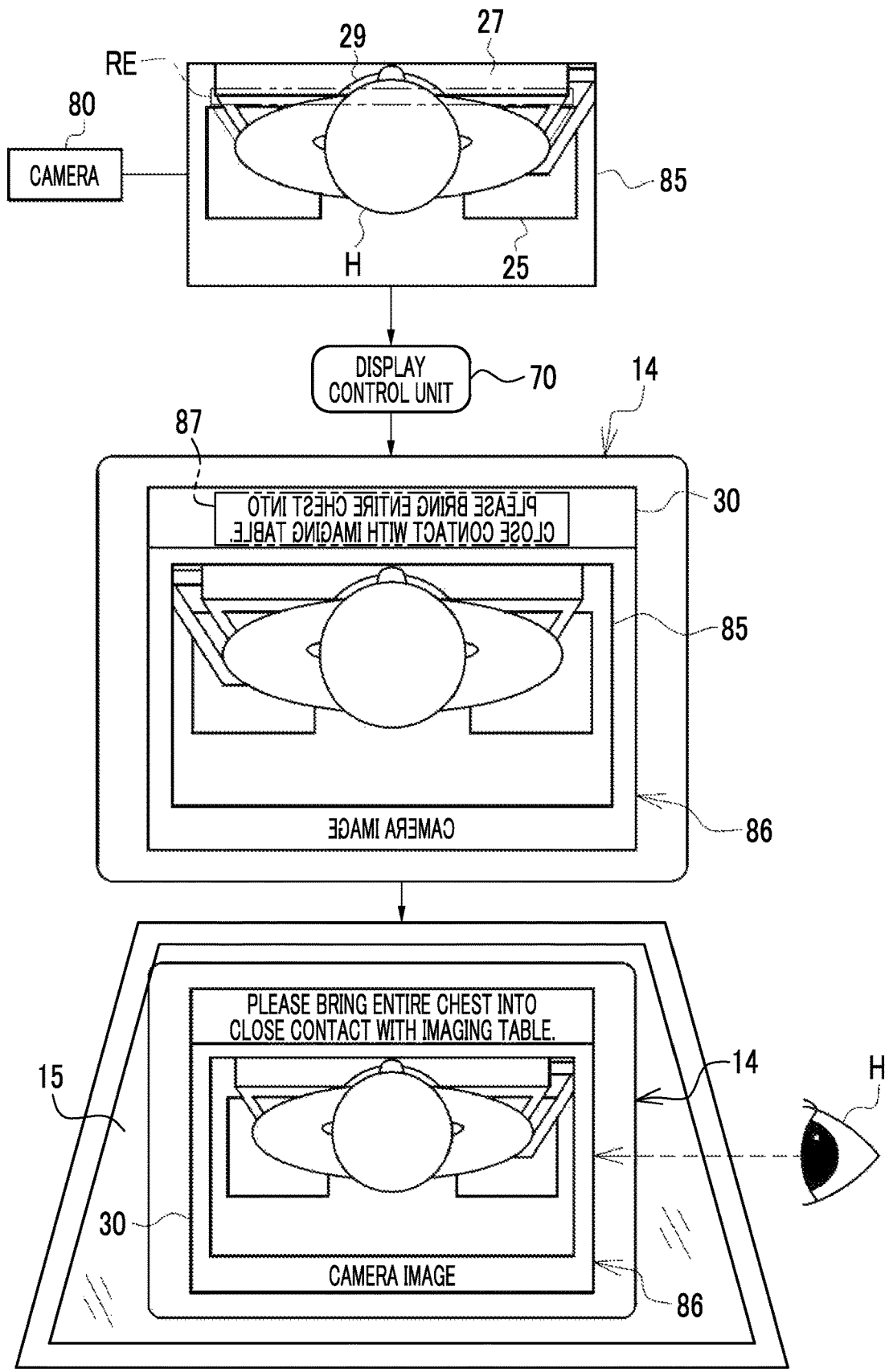
FIG. 10 is a diagram illustrating a process of a display control unit of a CPU of the console and a notification screen in the 2_1st embodiment.

For example, as illustrated in FIG. 10, the display control unit 70 acquires an image 85 output from the camera 80. The image 85 mainly includes the region RE at an angle from above. The image 85 is an example of the "detection result of the detection sensor" and "notification information" according to the technology of the present disclosure.

The display control unit 70 performs control to display a notification screen 86 on the touch panel display 30 of the tablet terminal 14. The notification screen 86 includes the image 85 and a guide message 87. Similarly to the image 71, the guide illustration 73, and the guide message 74 according to the first embodiment, both the images 85 and the guide message 87 are mirror-inverted such that they are reflected in the normal direction in a case in which they are reflected by the reflective member 15. The display control unit 70 displays the image 85 output from the camera 80 at a predetermined frame rate on the notification screen 86 while sequentially updating the image 85. That is, the image 85 displayed on the notification screen 86 is a live view image. The guide message 87 has content that prompts the subject H to bring the entire chest into close contact with the upright imaging stand 12.

In this case, the console 17 receives an instruction to switch the display of the notification screen 72 and the notification screen 86 from the operator OP through the input device 37. In a case in which the display switching instruction is received, the display control unit 70 switches one of the notification screen 72 and the notification screen 86 to the other.

The reflective member 15 reflects the touch panel display 30 of the tablet terminal 14 and thus the notification screen 86 such that the subject H standing in front of the upright imaging stand 12 can visually recognize the image 85 and the like.

As described above, in the 2_1st embodiment, the camera 80 that images the region RE including the boundary between the upright imaging stand 12 and the subject H standing in front of the upright imaging stand 12 is provided as the optical camera. Then, the image 85 which is output from the camera 80 and includes the region RE is displayed as the notification information. Therefore, the subject H can check the degree of close contact with the upright imaging stand 12 using the image 85. In a case in which the degree of close contact with the upright imaging stand 12 is small, there is a concern that the radiographic image will be unclear and reimaging will be unavoidable. Therefore, it is important to check the degree of close contact with the upright imaging stand 12 in determining the success or failure of radiography. Therefore, it is possible to display the notification information that is useful for the subject H himself or herself to take a posture suitable for radiography. In addition, the notification screen 86 may be displayed on the display 36 of the console 17 such that the operator OP also checks the degree of close contact of the subject H with the upright imaging stand 12.

Figure 11:
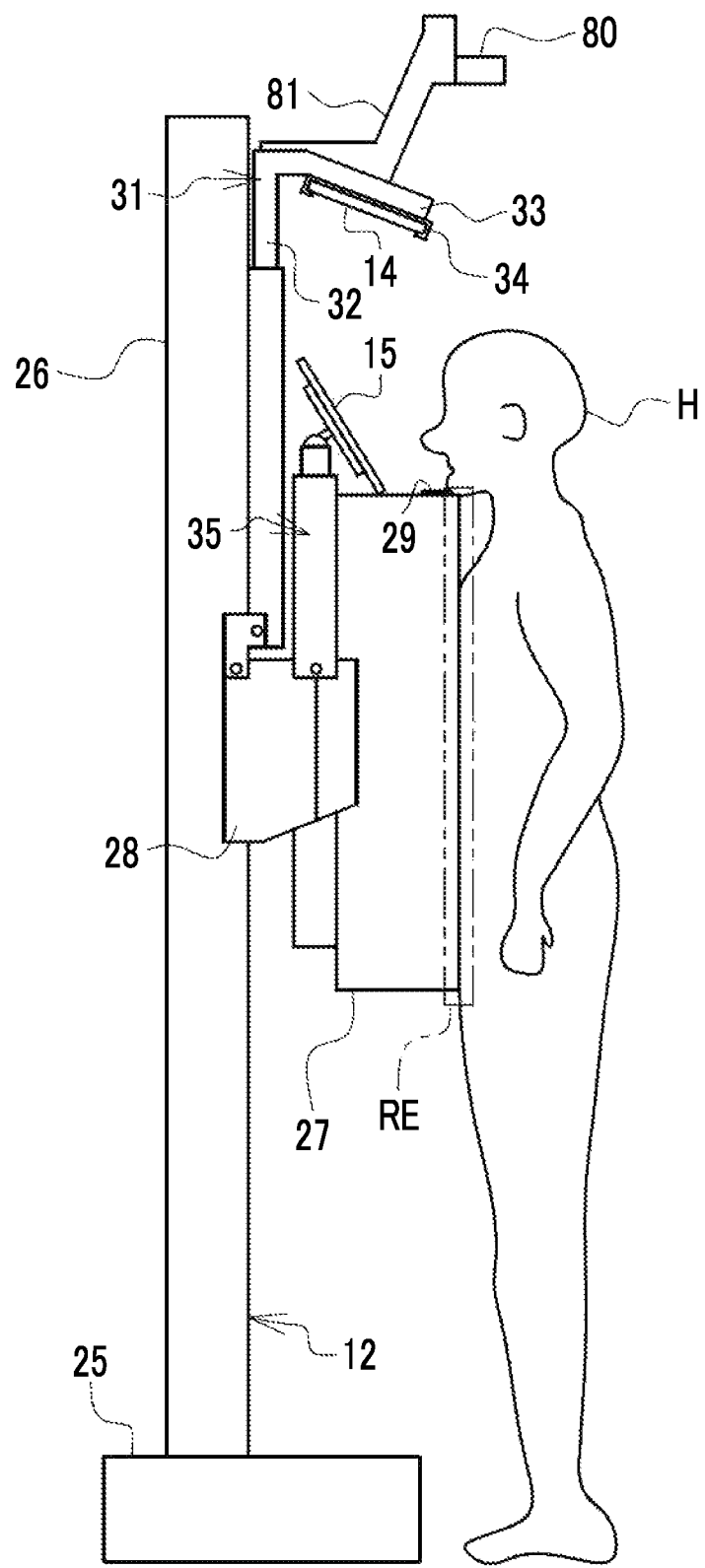
FIG. 11 is a diagram illustrating a modification example of the upright imaging stand according to the 2_1st embodiment.

For example, as illustrated in FIG. 11, the bending angle of the second portion 33 of the bracket 31 with respect to the first portion 32 may be an acute angle smaller than 90°. In this case, since the second portion 33, the terminal holder 34, and the tablet terminal 14 are retracted toward the support 26, it is possible to suppress the amount of protrusion of the other end of the bracket 81 obliquely upward, as compared to the case illustrated in FIG. 9.

Figure 12:
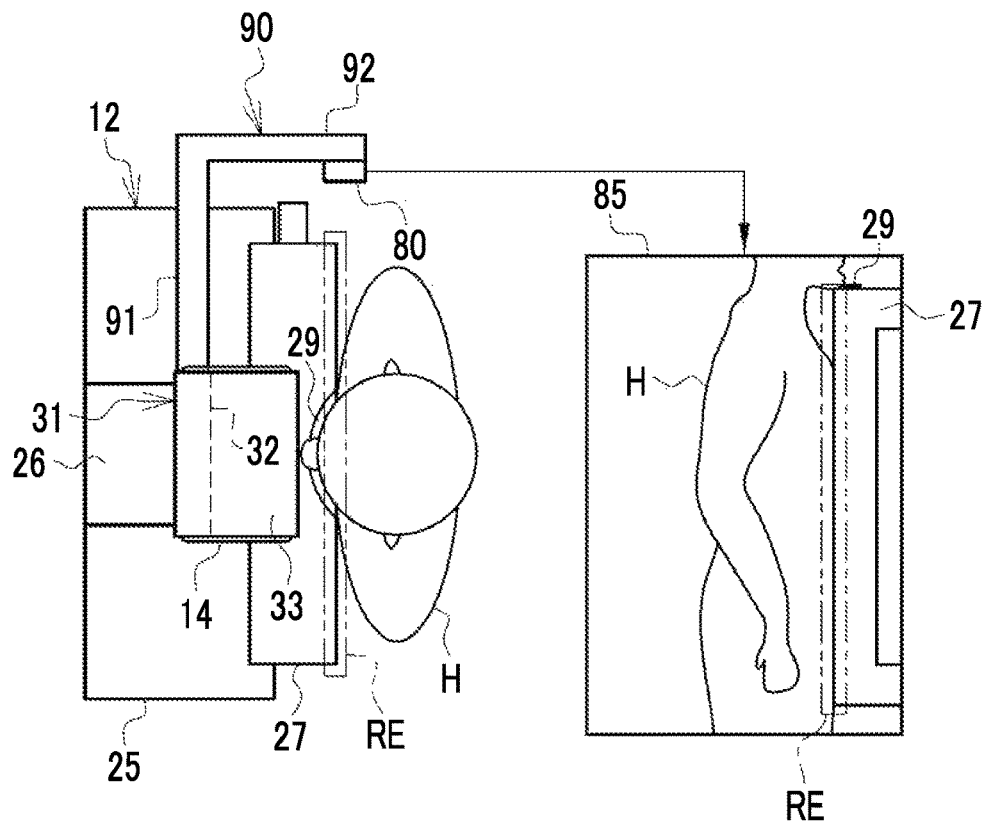
FIG. 12 is a diagram illustrating a modification example of the upright imaging stand according to the 2_1st embodiment.

In addition, for example, as illustrated in FIG. 12, the camera 80 may be disposed laterally, instead of being disposed about the head of the subject H. Specifically, the camera 80 is attached to a bracket 90. The bracket 90 has a first portion 91 that laterally extends from the first portion 32 of the bracket 31 and a second portion 92 that is bent 90° from the first portion 91 to the holder 27. A distal end of the second portion 92 faces the region RE. The camera 80 is attached to the distal end of the second portion 92. In this case, the image 85 output from the camera 80 mainly includes the region RE at an angle from the side. This configuration makes it possible to suppress the size of the upright imaging stand 12 in the height direction.

In addition, the aspect illustrated in FIG. 9 or FIG. 11 and the aspect illustrated in FIG. 12 may be combined with each other. That is, the image 85 including the region RE captured from the head of the subject H and the image 85 including the region RE captured from the side of the subject H may be displayed on the touch panel display 30 of the tablet terminal 14 to be switchable. In addition, the camera 80 may be attached to the ceiling of the radiography room 21. In this case, the height position of the camera 80 may be changed in operative association with the moving up and down of the holder 27, or the camera 80 may be mounted on the ceiling such that the height position is not changeable. Further, the camera 13 may not be provided, and only the camera 80 may be provided.

2_2nd Embodiment

Figure 13:
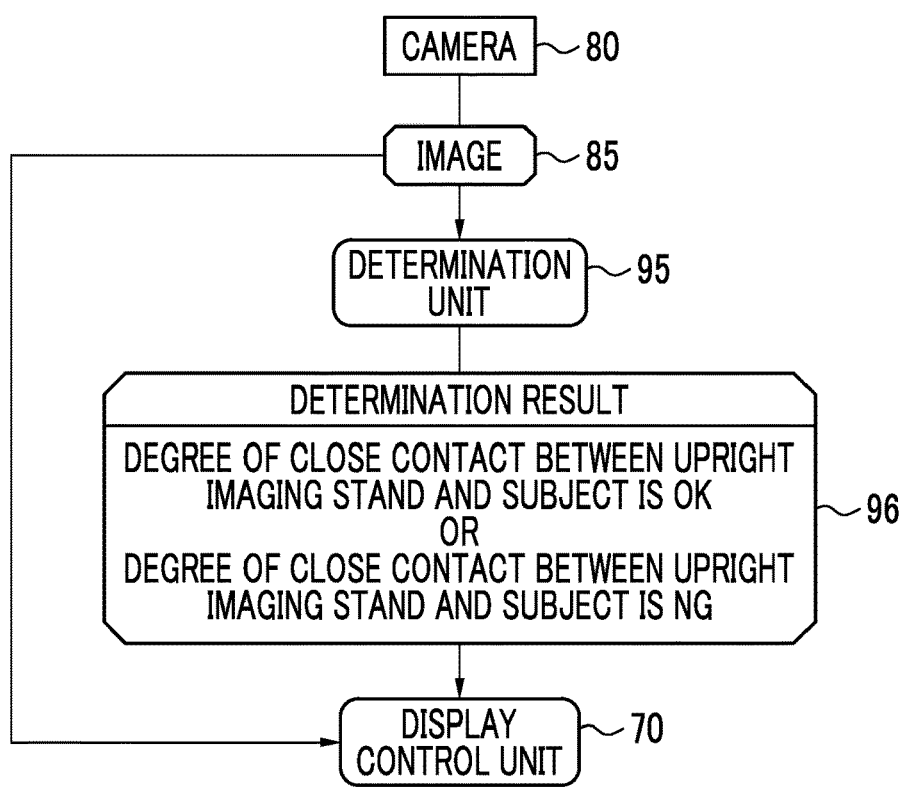
FIG. 13 is a diagram illustrating a process of a determination unit of a CPU of a console in a 2_2nd embodiment.

For example, as illustrated in FIG. 13, in a 2_2nd embodiment, the CPU 62 of the console 17 functions as a determination unit 95 in addition to the display control unit 70. The image 85 from the camera 80 is input to the determination unit 95. The determination unit 95 determines whether or not the degree of close contact between the upright imaging stand 12 and the subject H is suitable for radiography on the basis of the image 85. The degree of close contact between the upright imaging stand 12 and the subject H is an example of a "posture of the subject" according to the technology of the present disclosure.

For example, the determination unit 95 extracts the holder 27 and the shoulders of and the subject H from the image 85 using image recognition. Then, a numerical value indicating the degree of close contact of the subject H with the upright imaging stand 12 is derived from the positional relationship between the extracted holder 27 and shoulders of the subject H. In a case in which the derived numerical value is equal to or greater than a preset threshold value, the determination unit 95 determines that the degree of close contact between the upright imaging stand 12 and the subject H is suitable for radiography (the degree of close contact between the upright imaging stand and the subject is OK). On the other hand, in a case in which the derived numerical value is less than the threshold value, the determination unit 95 determines that the degree of close contact between the upright imaging stand 12 and the subject H is not suitable for radiography (the degree of close contact between the upright imaging stand and the subject is NG). The determination unit 95 outputs a determination result 96 to the display control unit 70.

Figure 14:
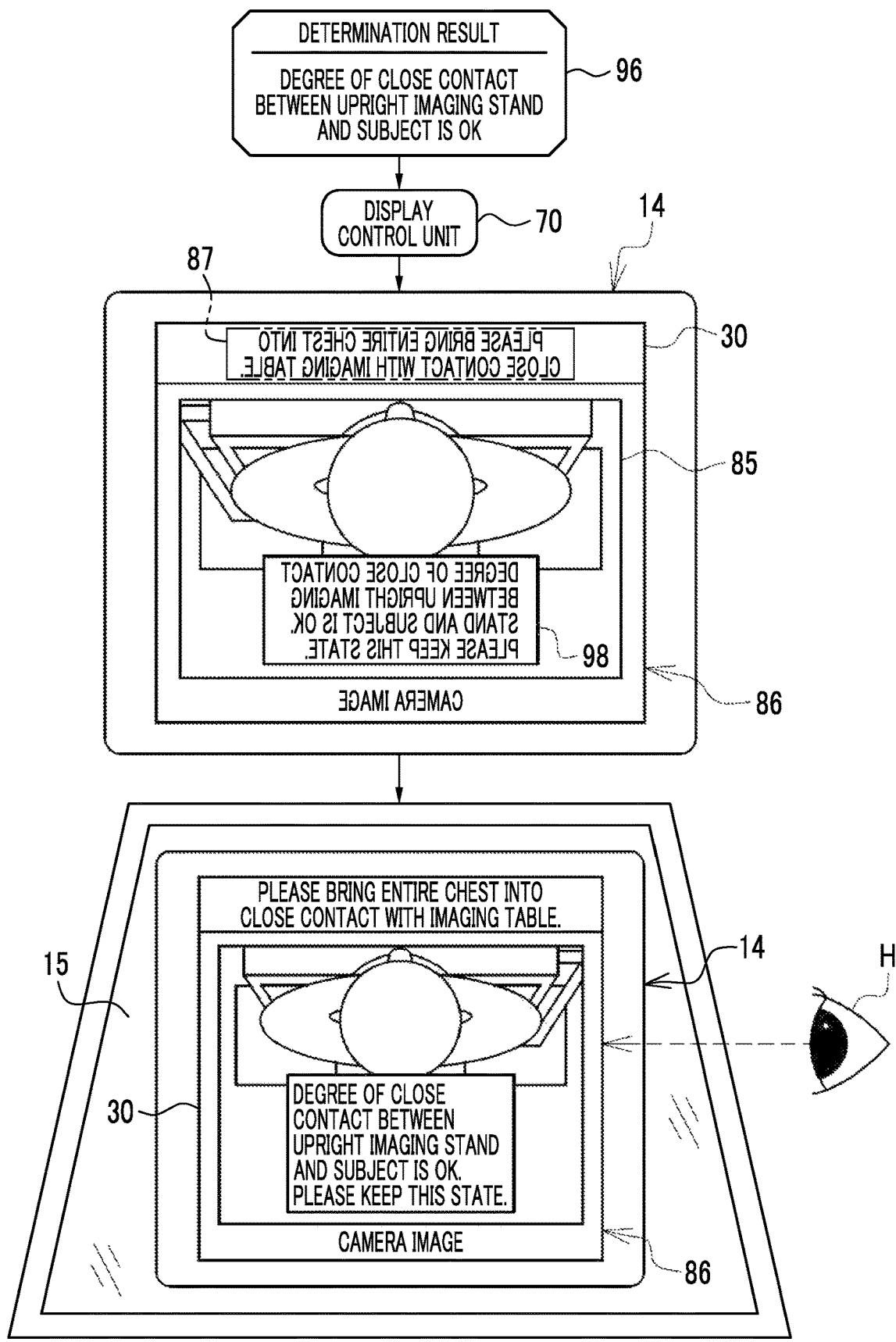
FIG. 14 is a diagram illustrating a process of a display control unit of the CPU of the console and a notification screen in the 2_2nd embodiment.

For example, as illustrated in FIG. 14, the display control unit 70 displays a message 98 indicating the determination result 96 on the notification screen 86 in addition to the image 85 and the guide message 87. Similarly to the image 85 and the like, the message 98 is also mirror-inverted such that it is reflected in the normal direction in a case in which it is reflected by the reflective member 15. FIG. 14 illustrates a case in which the determination result 96 shows that the degree of close contact between the upright imaging stand 12 and the subject H is suitable for radiography. In a case in which the determination result 96 shows that the degree of close contact between the upright imaging stand 12 and the subject H is not suitable for radiography, a message 98 that prompts the subject to further come into close contact with the upright imaging stand 12 is displayed, which is not illustrated.

As described above, in the 2_2nd embodiment, the determination result 96, which has been determined by the determination unit 95 on the basis of the image 85 output from the camera 80 and indicates whether or not the degree of close contact between the upright imaging stand 12 and the subject H is suitable for radiography, is displayed as notification information on the touch panel display 30 of the tablet terminal 14. Therefore, in a case in which the determination result 96 shows that the degree of close contact between the upright imaging stand 12 and the subject H is suitable for radiography, it is possible to make the subject H maintain the posture suitable for radiography. On the other hand, in a case in which the determination result 96 shows that the degree of close contact between the upright imaging stand 12 and the subject H is not suitable for radiography, it is possible to strongly encourage the subject H to improve the degree of close contact with the upright imaging stand 12.

The detection sensor is not limited to the optical camera. For example, as illustrated in FIGS. 15 and 16, a distance measuring sensor 100 may be used as the detection sensor.

Figure 15:
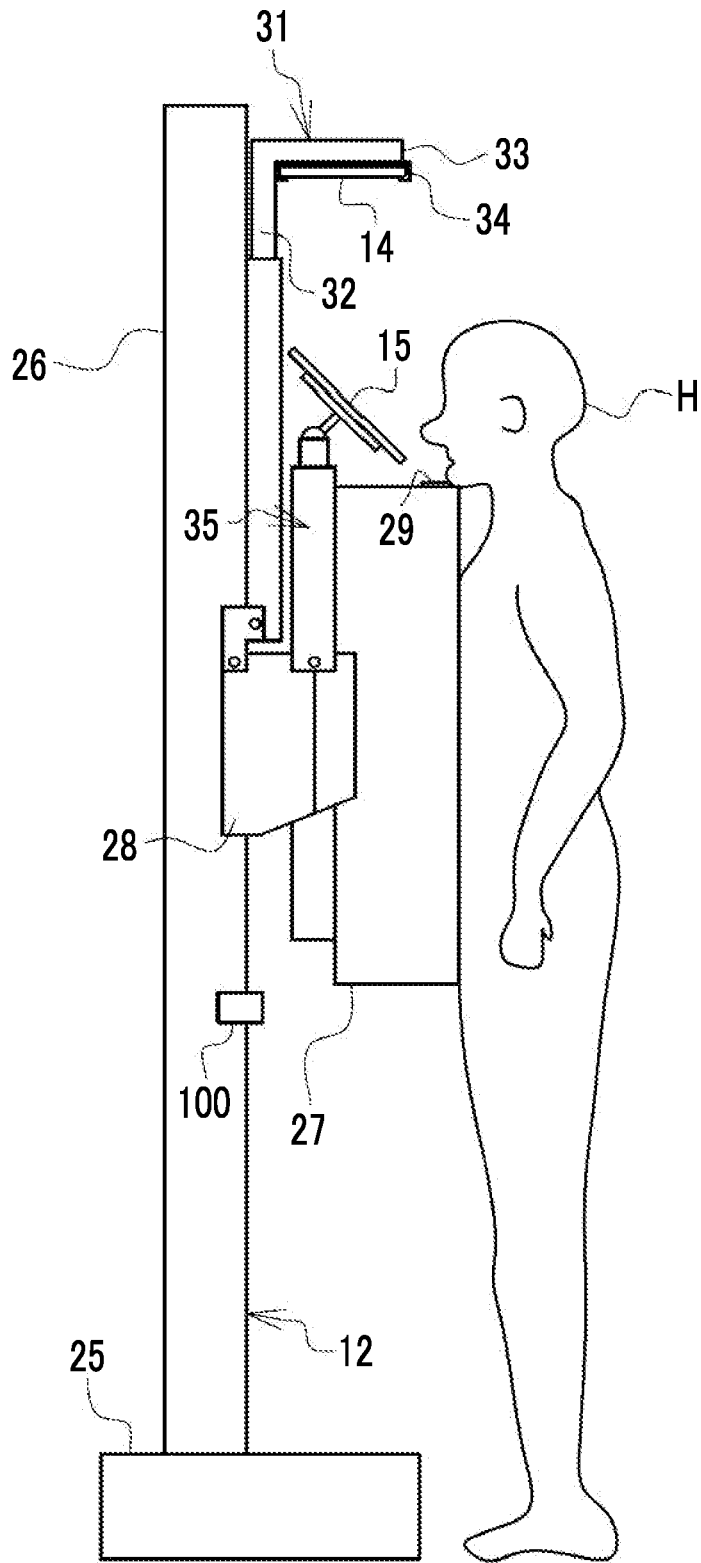
FIG. 15 is a diagram illustrating an example in which a distance measuring sensor is used as a detection sensor.

In FIG. 15, the distance measuring sensor 100 is attached to the lower portion of the support 26. The distance measuring sensor 100 is, for example, a time-of-flight (TOF) camera, a visible light stereo camera, an infrared stereo camera, a laser displacement meter, a light detection and ranging (LIDAR) camera, an ultrasound length measuring device, and the like and measures the distance of the subject H, who stands in front of the upright imaging stand 12, from the support 26.

Figure 16:
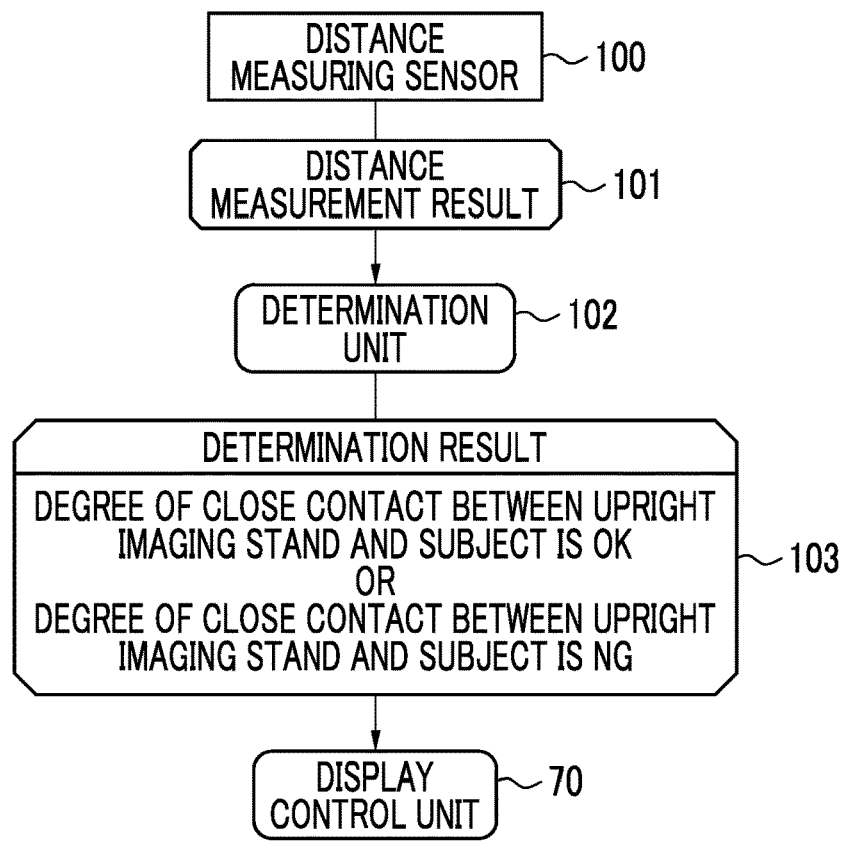
FIG. 16 is a diagram illustrating a process of a determination unit of the CPU of the console in a case in which the distance measuring sensor is used as the detection sensor.

For example, as illustrated in FIG. 16, a distance measurement result 101 of the distance measuring sensor 100 is input to a determination unit 102. The determination unit 102 compares the distance measurement result 101 with a preset threshold value. In a case in which the distance measurement result 101 is less than the threshold value, the determination unit 102 determines that the degree of close contact between the upright imaging stand 12 and the subject H is suitable for radiography (the degree of close contact between the upright imaging stand and the subject is OK). On the other hand, in a case in which the distance measurement result 101 is equal to or greater than the threshold value, the determination unit 102 determines that the degree of close contact between the upright imaging stand 12 and the subject H is not suitable for radiography (the degree of close contact between the upright imaging stand and the subject is NG). The determination unit 102 outputs a determination result 103 to the display control unit 70. Similarly to the notification screen 86 illustrated in FIG. 14, the display control unit 70 displays a notification screen, on which a message corresponding to the determination result 103 has been displayed, on the touch panel display 30 of the tablet terminal 14.

As described above, the detection sensor is not limited to the optical camera and may be the distance measuring sensor 100. In addition, as the detection sensor, a pressure sensor may be provided in the holder 27, and it may be determined whether or not the degree of close contact between the upright imaging stand 12 and the subject H is suitable for radiography on the basis of a detection result of the pressure sensor.

Figure 17:
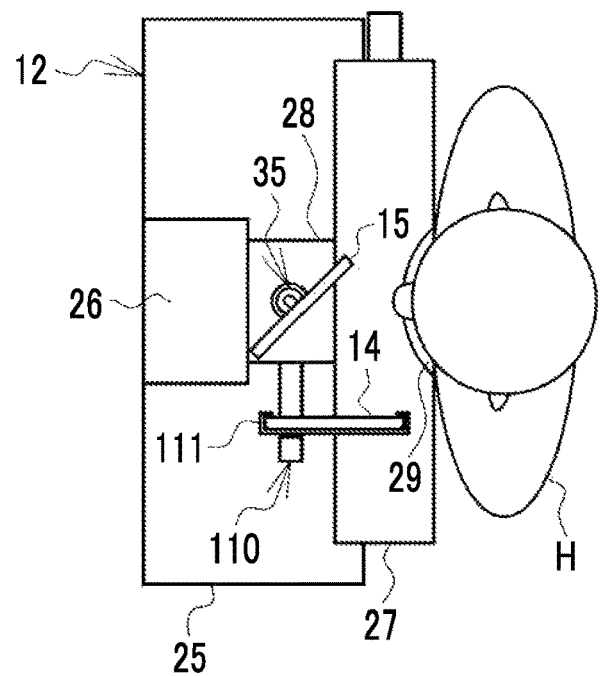
FIG. 17 is a diagram illustrating an example in which the tablet terminal is disposed obliquely in front of a face of a subject standing in front of the upright imaging stand.

In each of the above-described embodiments, the position above the head of the subject H is given as an example of the position where the tablet terminal 14 is disposed not to interfere with the subject H in a case in which the subject H stands in front of the upright imaging stand 12. However, the present disclosure is not limited thereto. For example, as illustrated in FIG. 17, the tablet terminal 14 may be disposed obliquely in front of the face of the subject H standing in front of the upright imaging stand 12. Specifically, the tablet terminal 14 is attached to a terminal holder 111 of a bracket 110. The bracket 110 is attached to the connection portion 28, and a distal end of the bracket 110 having the terminal holder 111 is positioned obliquely in front of the face of the subject H. In this case, the reflective member 15 is inclined laterally (toward the tablet terminal 14) by 45° with respect to the line of sight of the subject H. This configuration makes it possible to suppress the size of the upright imaging stand 12 in the height direction.

Figure 18:
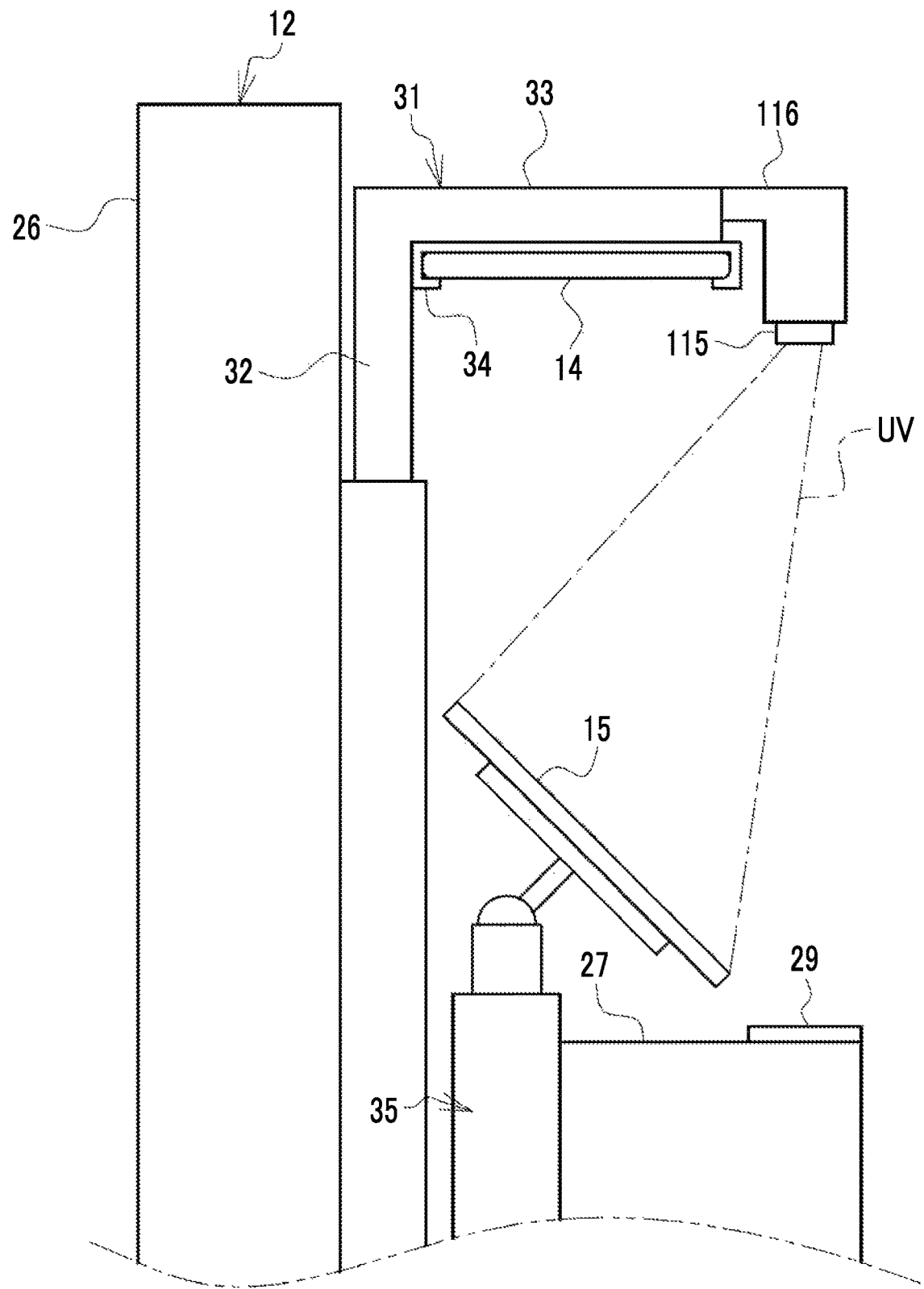
FIG. 18 is a diagram illustrating an example in which an ultraviolet source that irradiates a surface of a reflective member with ultraviolet rays is provided.

For example, as illustrated in FIG. 18, an ultraviolet source 115 that irradiates the surface of the reflective member 15 exposed to the breath of the subject H with ultraviolet rays UV may be provided. The ultraviolet source 115 is attached to a bracket 116 that extends from the distal end of the second portion 33 of the bracket 31. This makes it possible to disinfect the surface of the reflective member 15 exposed to the breath of the subject H with the ultraviolet rays UV.

In this case, for example, the image 71 of the camera 13 is analyzed to detect whether or not the subject H is present in the vicinity of the upright imaging stand 12. Then, in a case in which it is detected that the subject H is not present in the vicinity of the upright imaging stand 12, the ultraviolet rays UV may be emitted from the ultraviolet source 115. In addition, instead of or in addition to the ultraviolet source 115, an ozone ejector or an ejector for a disinfectant, such as hypochlorous acid water, may be provided to disinfect the surface of the reflective member 15. A mechanism may be provided which automatically disinfects not only the reflective member 15 but also the surface of the chin rest portion 29 with which the chin of the subject H comes into contact or the surface of the holder 27 with which the chest of the subject H comes into close contact.

Figure 19:
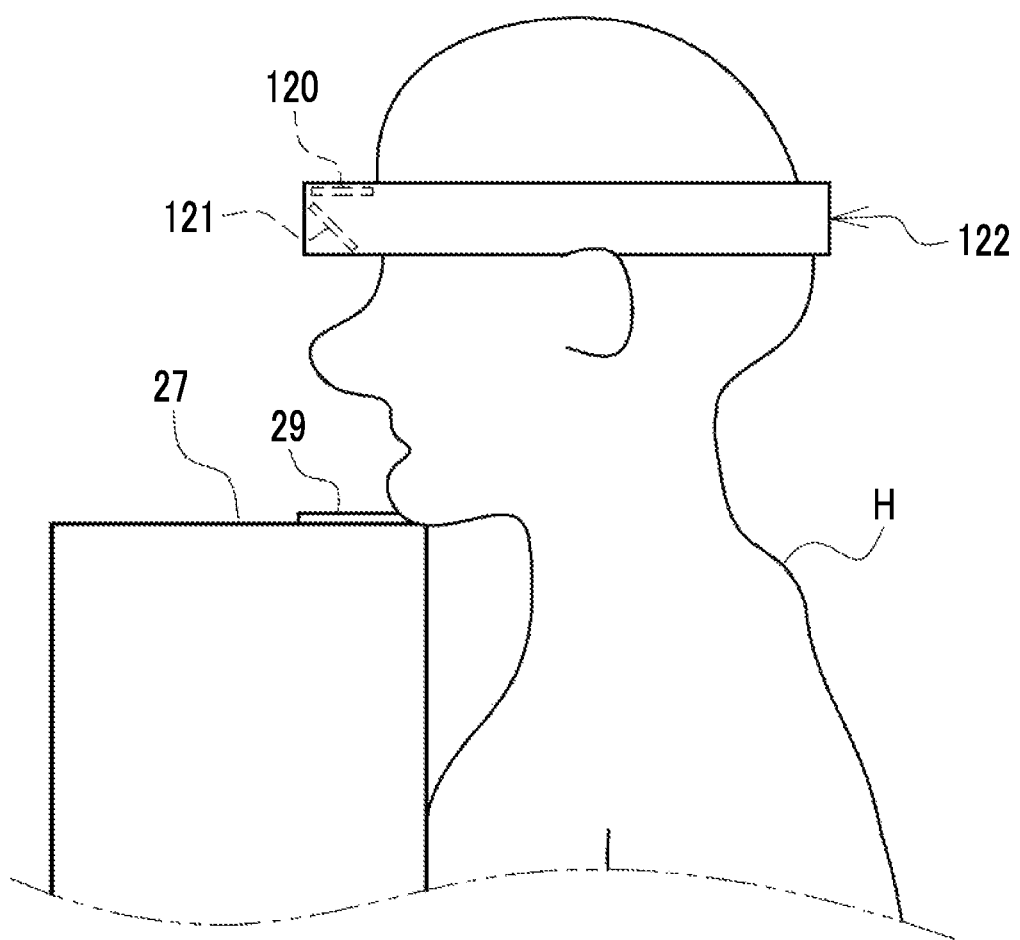
FIG. 19 is a diagram illustrating an example in which a head-mounted display in which a display and a reflective member are integrally incorporated is attached to the subject.

For example, as illustrated in FIG. 19, a head-mounted display 122 in which a display 120 as the display and a reflective member 121 are integrally incorporated may be attached to the subject H. This makes it possible to simplify the configuration of the upright imaging stand 12 as compared to each of the above-described embodiments in which the tablet terminal 14 and the reflective member 15 are attached to the upright imaging stand 12.

The display is not limited to the tablet terminal 14. A display that simply has only a display function may be used.

The electronic cassette is given as an example of the radiographic image detector. However, the present disclosure is not limited thereto. A radiographic image detector that is provided in the upright imaging stand 12 may also be used. Further, the imaging table is not limited to the upright imaging stand 12. The imaging table may be a sitting imaging stand for radiography on the subject H in a sitting posture or a decubitus imaging table for radiography on the subject H in a decubitus posture.

In addition, the reflective member 15 may be formed integrally with the holder 27. However, as in each of the above-described embodiments, it is preferable that the reflective member 15 is provided separately from the holder 27 and is attached to the holder 27 by the bracket 35 in order to facilitate manufacture.

In each of the above-described embodiments, for example, the following various processors can be used as a hardware structure of processing units performing various processes, such as the display control unit 70 and the determination units 95 and 102. The various processors include, for example, the CPU 62 which is a general-purpose processor executing software (operation program 65) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of ASICs and/or a combination of an ASIC and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by using one or more of the various processors as a hardware structure.

Furthermore, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other. In addition, the present disclosure is not limited to each of the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, in the content described and illustrated above, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference herein to the same extent as each individual document, each patent application, and each technical standard are specifically and individually stated to be incorporated by reference.

What is claimed is:

1. A radiography apparatus comprising:
an imaging table that is used for radiography on a subject;
a detection sensor that detects a state of the subject with respect to the imaging table;
a display that displays a notification screen including notification information based on a detection result of the detection sensor; and
a reflective member that reflects the notification screen such that the subject facing the imaging table visually recognizes the notification information.

2. The radiography apparatus according to claim 1,
wherein the detection sensor is an optical camera that images the subject facing the imaging table, and
the notification information is at least one of an image output from the optical camera or a determination result which has been determined on the basis of the image output from the optical camera and which indicates whether or not a posture of the subject is suitable for the radiography.

3. The radiography apparatus according to claim 2,
wherein the optical camera includes a first camera that images a back surface of the subject facing the imaging table.

4. The radiography apparatus according to claim 3,
wherein the first camera is attached to a radiation source that emits radiation.

5. The radiography apparatus according to claim 2,
wherein the optical camera includes a second camera that images a region including a boundary between the imaging table and the subject facing the imaging table.

6. The radiography apparatus according to claim 1,
wherein the display is disposed at a position that does not interfere with the subject in a case in which the subject faces the imaging table, and
the reflective member is disposed in front of a face of the subject facing the imaging table.

7. The radiography apparatus according to claim 1,
wherein the imaging table has a holder that holds a radiographic image detector which detects radiation and which outputs a radiographic image and that is moved in accordance with a physique of the subject, and
the display and the reflective member are provided in the holder.

8. The radiography apparatus according to claim 1, further comprising:
an adjustment mechanism that adjusts a position and orientation of the reflective member with respect to the subject.

9. The radiography apparatus according to claim 1,
wherein the display is attachable to and detachable from the imaging table.

10. The radiography apparatus according to claim 1,
wherein the reflective member is any one of a glass plate or a resin plate having a metal film formed on a surface thereof, a metal plate having a mirror-finished surface, or a plate having a highly reflective film attached thereto.

11. The radiography apparatus according to claim 1,
wherein a transparent cover for protecting a surface of the reflective member is provided.

12. The radiography apparatus according to claim 1,
wherein a frame is attached to an entire periphery of the reflective member.

13. The radiography apparatus according to claim 1,
wherein the imaging table is an upright imaging stand used for the radiography on the subject in a standing posture.

* * * * *